US010632227B2

(12) United States Patent
Ren et al.

(10) Patent No.: US 10,632,227 B2
(45) Date of Patent: Apr. 28, 2020

(54) METHOD OF MAKING INJECTABLE CEMENTS

(71) Applicant: Wayne State University, Detroit, MI (US)

(72) Inventors: Weiping Ren, Westland, MI (US); Wei Song, Warren, MI (US)

(73) Assignee: Wayne State University, Detroit, MI (US)

(*) Notice: Subject to any disclaimer, the term of this patent is extended or adjusted under 35 U.S.C. 154(b) by 146 days.

(21) Appl. No.: 15/548,389

(22) PCT Filed: Feb. 8, 2016

(86) PCT No.: PCT/US2016/016979
§ 371 (c)(1),
(2) Date: Aug. 2, 2017

(87) PCT Pub. No.: WO2016/130468
PCT Pub. Date: Aug. 18, 2016

(65) Prior Publication Data
US 2018/0015198 A1 Jan. 18, 2018

Related U.S. Application Data

(60) Provisional application No. 62/113,798, filed on Feb. 9, 2015.

(51) Int. Cl.
*A61L 24/00* (2006.01)
*A61L 24/02* (2006.01)
*C04B 28/34* (2006.01)
*C04B 12/02* (2006.01)

(52) U.S. Cl.
CPC ....... *A61L 24/0063* (2013.01); *A61L 24/0052* (2013.01); *A61L 24/02* (2013.01); *C04B 12/02* (2013.01); *C04B 12/025* (2013.01); *C04B 28/34* (2013.01); *A61L 2400/06* (2013.01); *A61L 2430/02* (2013.01)

(58) Field of Classification Search
CPC .. A61L 24/02; A61L 24/0052; A61L 24/0063; A61L 2400/02; A61L 2430/06; C04B 12/02; C04B 12/025; C04B 28/34
See application file for complete search history.

(56) References Cited

U.S. PATENT DOCUMENTS

| | | |
|---|---|---|
| 2002/0136696 A1 | 9/2002 | Lee et al. |
| 2004/0043051 A1 | 3/2004 | Pilliar et al. |
| 2004/0043501 A1 | 3/2004 | Means et al. |
| 2004/0112256 A1 | 6/2004 | Tas |
| 2007/0113951 A1 | 5/2007 | Huang |
| 2007/0178309 A1 | 8/2007 | Omelon |
| 2007/0238835 A1* | 10/2007 | Chen .............. C08L 53/02 525/240 |
| 2010/0040668 A1 | 2/2010 | Riman et al. |
| 2011/0064703 A1 | 3/2011 | Kumta et al. |
| 2013/0039990 A1 | 2/2013 | Xu et al. |
| 2013/0121956 A1 | 5/2013 | Barralet et al. |
| 2015/0290361 A1* | 10/2015 | Puleo .............. A61L 27/18 514/154 |

FOREIGN PATENT DOCUMENTS

| | | | |
|---|---|---|---|
| CN | 101402736 A | 4/2009 | |
| CN | 101444640 A1 | 6/2009 | |
| WO | WO 2015/003140 A1 | 1/2015 | |
| WO | WO-2016012583 A1 * | 1/2016 | ............. A61L 27/20 |

OTHER PUBLICATIONS

Machine Translation of Chinese Patent Specification No. CN 101402736 A (Year: 2009).*
Search Report and Written Opinion dated Mar. 23, 2016.
Extended European Search Report dated Sep. 19, 2018.
International Search Report for PCT/US2014/045423 dated Oct. 24, 2014.
Grynpas MD, Pilliar RM, Kandel RA, Renlund R, Filiaggi M, Dumitriu M. "Porous calcium polyphosphate scaffolds for bone substitute applications in vivo studies." *Biomaterials* May 2002; 23(9) pp. 2063-2070.
Hench LL, West JK. "The Sol-Gel Process." *Chemical Reviews* 90(1) pp. 33-72. (1990).
Pilliar RM et al. "Porous calcium polyphosphate scaffolds for bone substitute applications—in vitro characterization." *Biomaterials* 22 pp. 963-972 (2001).
Song W, Wang Q, Wan C, Shi T, Markel D, Blaiser R, Ren W. "A novel alkali metals/strontium co-substitued calcium polyphosphate scaffolds in bone tissue engineering." *Journal of Biomedical Materials Research* vol. 98B, issue 2, pp. 255-262 (Aug. 2011).
Song W, Ren W, Wan C, Esequivel AO, Shi T, Blasier R, Markel DC. "A novel strontium-doped calcium polyphosphate/erythromycin/poly(vinyl alchohol) composite for bone tissue engineering." *J Biomed Mater Res A*. 98(3), pp. 359-371 (Sep. 2011).
Dion A et al. "The effect of processing on the structural characteristics of vancomycin-loaded amorphous calcium phosphate matrices." *Biomaterials*, vol. 26, No. 21, pp. 4486-4494 (Jul. 2005).
Kasuga T. et al. "Hydrogelation of calcium metaphosphate glass." *Chemistry Letters, Chemical Society of Japan*, Aug. 2001, pp. 820-821.

(Continued)

*Primary Examiner* — Anthony J Green
(74) *Attorney, Agent, or Firm* — Fishman Stewart PLLC

(57) ABSTRACT

A discovery of the conversion of amorphous calcium polyphosphate (ACPP) or/and other polyphosphate salts with various type of calcium phosphate to new calcium phosphate product (i.e. dicalcium phosphate dihydrate (DCPD)) in a liquid environment. The discovery includes mixing a various type of calcium phosphate with an aqueous ACPP or/and other polyphosphate salts gel, which is fast setting and possessing strong mechanical strength, and can be gradually converted to DCPD/hydroxyapatites in physiological condition. This injectable past can be applied as alternative of conventional CPC bone cement that is suitable for bone void repair due to its excellent properties in osteoconductivity and osseointegration. It can also be applied as drug delivery device in tissue engineering for its strong bonding to drug molecules.

20 Claims, 11 Drawing Sheets

(56) References Cited

OTHER PUBLICATIONS

Kopp, Willian, "Calcium polyphosphate coacervates: effects of thermal treatment," J Sol-Gel Sci Technol, 2011, Springer Science Business Media.
European Search Report in Application No. 14820397.9, dated Jan. 31, 2017.

* cited by examiner

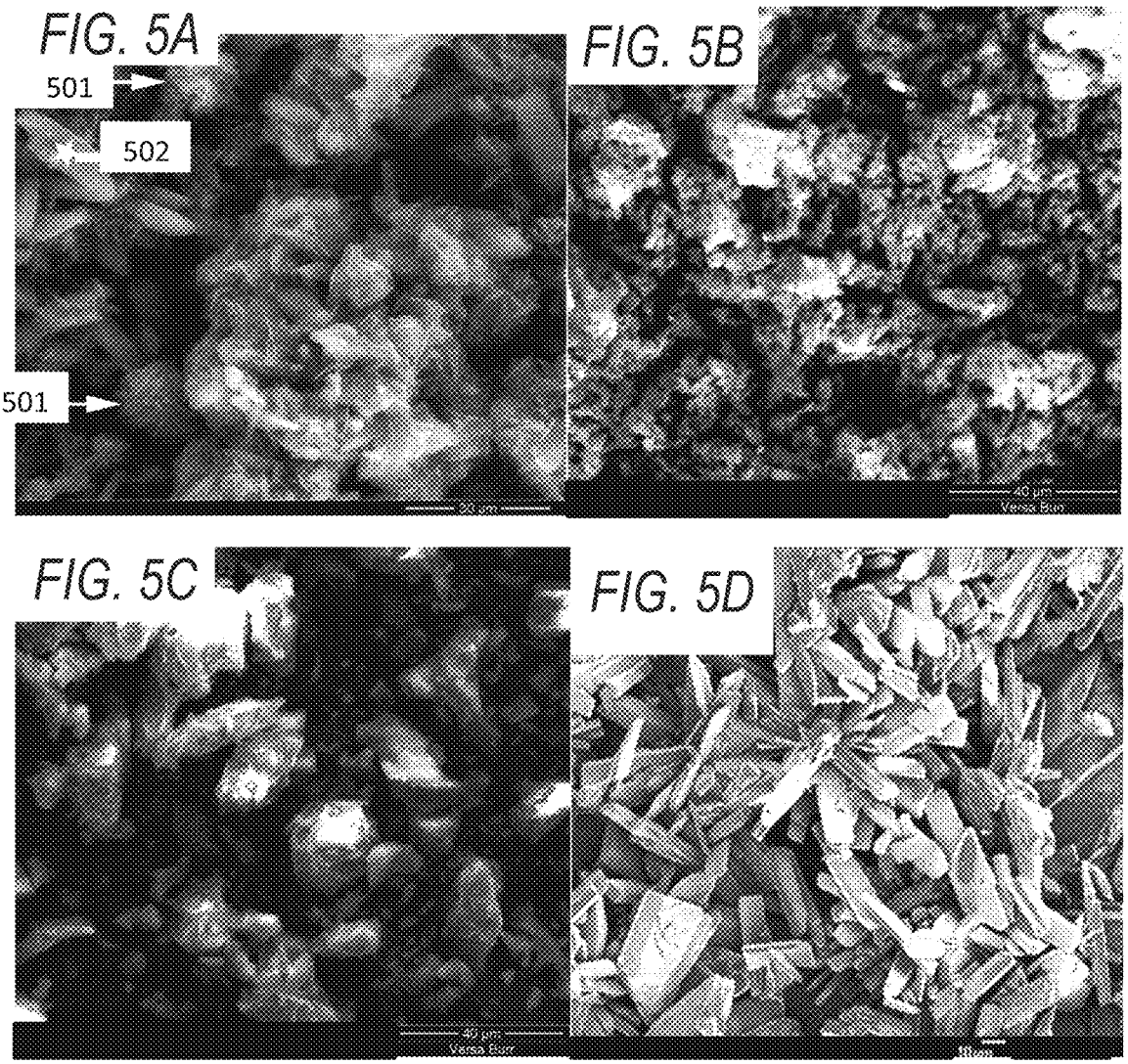

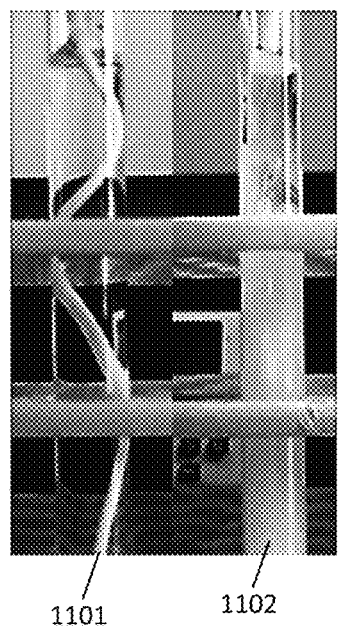
FIG. 11A  FIG. 11B
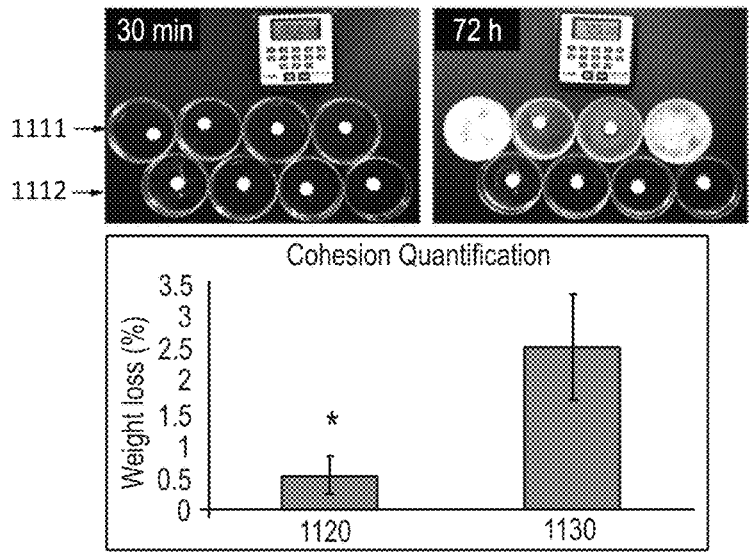
FIG. 11C  FIG. 11D
FIG. 11E
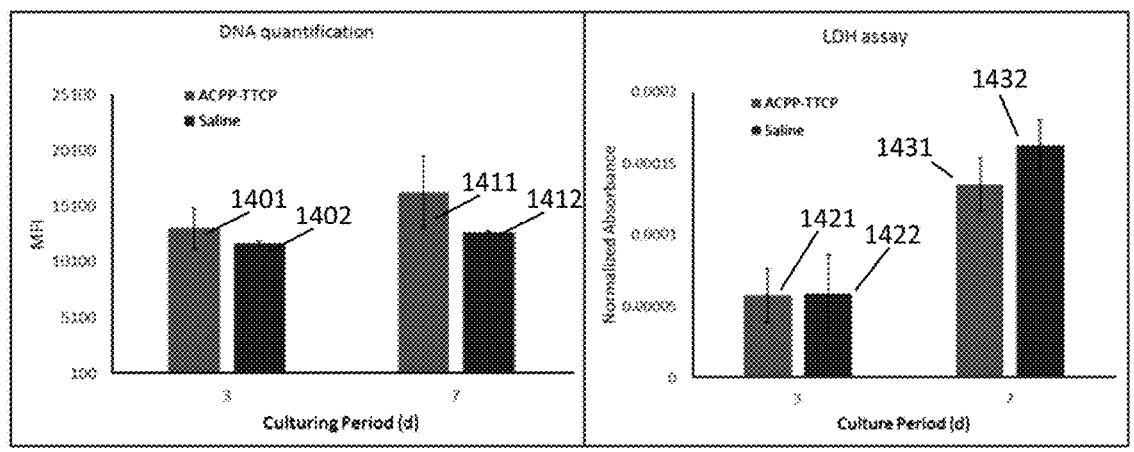
FIG. 14A  FIG. 14B

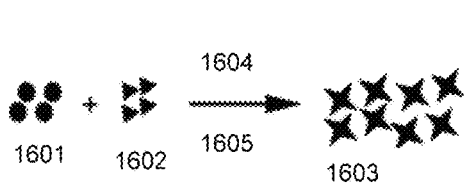
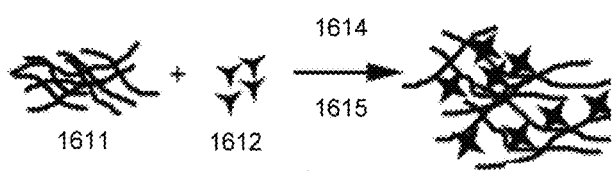
FIG. 16A
FIG. 16B
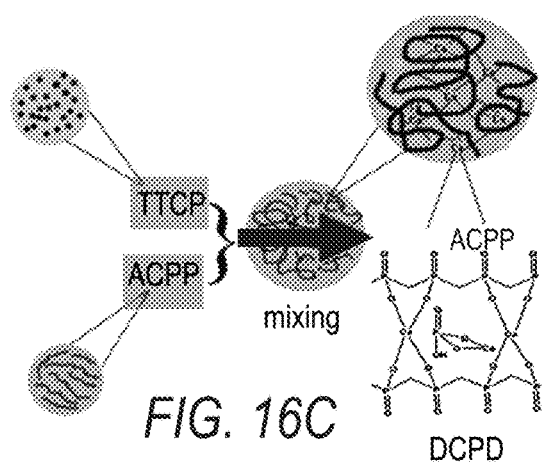
FIG. 16C
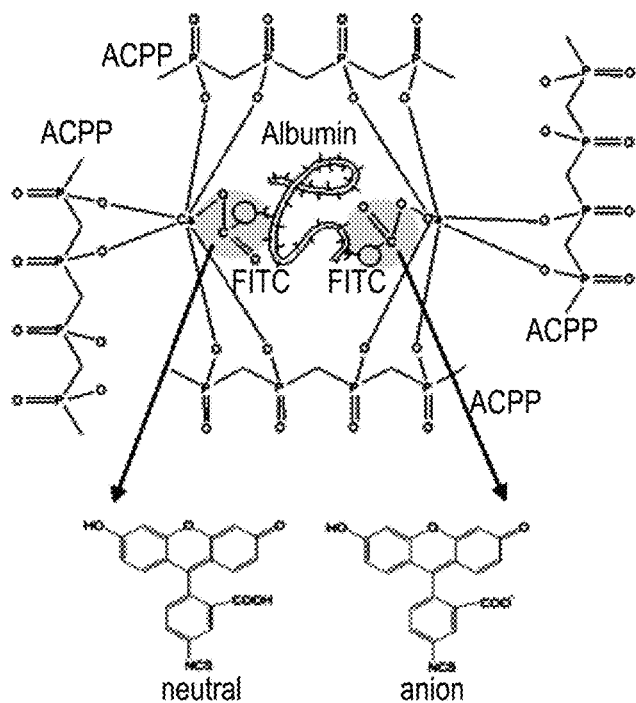
FIG. 16D

METHOD OF MAKING INJECTABLE CEMENTS

This application is a 371 national stage application of PCT/US2016/016979, filed Feb. 9, 2016, entitled "METHOD OF MAKING INJECTABLE CEMENTS," which application claims priority to U.S. Provisional Patent Application Ser. No. 62/113,798, filed Feb. 9, 2015, entitled "METHOD OF MAKING INJECTABLE CEMENTS," the entire contents of each of which are incorporated herein by reference.

BACKGROUND

Technical Field

The present invention relates to injectable cements for the repair of bones. More particularly, the present invention provides a composition of matter and a method for making an injectable bone cement comprising a polyphosphate compound and a source of calcium and phosphate, optionally including at least one or more inorganic fillers and one or more organic fillers.

Background Information

Despite years of effort, researchers have been unable to provide calcium phosphate cement (CPC) bone graft substitutes performing well enough to replace bone grafting procedures. Though numerous CPCs are on the market, they suffer from having limited osteogenesis potential, unacceptable levels of brittleness after settling, low mechanical strength, and burst drug release.

Two main types of material are currently used in bone-repair applications, each with their own limitations: acrylic-based bone cement (PMMA) can generate toxic debris as it wears, has poor adherence to bone, and generates heat during its exothermic curing process; and calcium phosphate cement (CPC) is limited due to the use of phosphoric solution as initiator to react with calcium phosphate salts. Most CPC exhibits suboptimal mechanical strength, brittleness and drug delivery capability.

There is a need to develop bone cements with better mechanical properties and which can provide more consistent release of medicaments and other substances, for example stem cells.

BRIEF SUMMARY

In one aspect, a cement is provided. A cement is made from at least a first compound which is, at least in part, a hydrogel including a polyphosphate, and a second compound which is a source of calcium and phosphate. The cement has a viscosity number for injectability and has a setting temperature less than about 80 degrees Celsius. The cement is injectable, and is tunable in mechanical strength for both load-bearing and non-load-bearing bone repair applications.

In another aspect, a method of making a cement is provided which includes steps of gelating of a first polyphosphate compound in aqueous solution to form a hydrogel; and reacting the hydrogel with a second compound comprising calcium and phosphate to form an injectable bone cement. The method may further comprise mixing a filler material with the first polyphosphate compound, the filler material comprising at least one of an inorganic material and an organic material. The second compound may comprise at least one of an amorphous calcium phosphate ceramic, an α-type calcium phosphate ceramic, an β-type calcium phosphate ceramic, a γ-type calcium phosphate ceramic, hydroxyapatite, calcium polyphosphate, octacalcium phosphate, tricalcium phosphate, amorphous calcium phosphate, monocalcium phosphate monohydrate, anhydrous monocalcium phosphate, dicalcium phosphate dihydrate (brushite), anhydrous dicalcium phosphate (monetite), and tetracalcium phosphate. The first polyphosphate compound may comprise at least one of sodium polyphosphate, potassium polyphosphate, calcium polyphosphate, strontium polyphosphate, magnesium polyphosphate, aluminum polyphosphate, zinc polyphosphate, copper polyphosphate, cadmium polyphosphate, manganese polyphosphate, ammonium polyphosphate, and chelated composites and blends thereof. The first polyphosphate compound may comprise amorphous calcium polyphosphate and the second compound may comprise tetracalcium phosphate.

BRIEF DESCRIPTION OF THE DRAWINGS

FIG. 5 is a scanning electron microscope image of the ACPP/TTCP cement conversion to DCPD after incubation at 37 degrees Celsius during 4 weeks for demonstration of the final product crystalline structure in accordance with one aspect of the present invention;

FIG. 11A is a photograph of a cement of the present invention after mixing and injection into a cylinder of water;

FIG. 11B is a photograph of a prior art cement after mixing and injection into a cylinder of water;

FIGS. 11C and 11D are photographs of a cohesion test of materials of the present invention compared with prior art materials at about 30 minutes and about 72 hours, respectively, after immersion in phosphate-buffered saline (PBS);

FIG. 11E is a bar graph quantifying the results of the assay shown in FIGS. 11C and 11D;

FIGS. 14A and 14B are bar graphs of the results of a cell culture experiment in accordance with an ASTM standard;

FIG. 16A is a schematic illustration of the mechanism of formation of a prior art material;

FIGS. 16B and 16C are schematic illustrations of mechanisms of formation of a material according to embodiments of the present invention; and FIG. 16D is a schematic illustration of the mechanism of interaction between a material according to an embodiment of the present invention with a protein.

DETAILED DESCRIPTION OF THE DRAWINGS AND THE PRESENTLY PREFERRED EMBODIMENTS

Figure 1A:
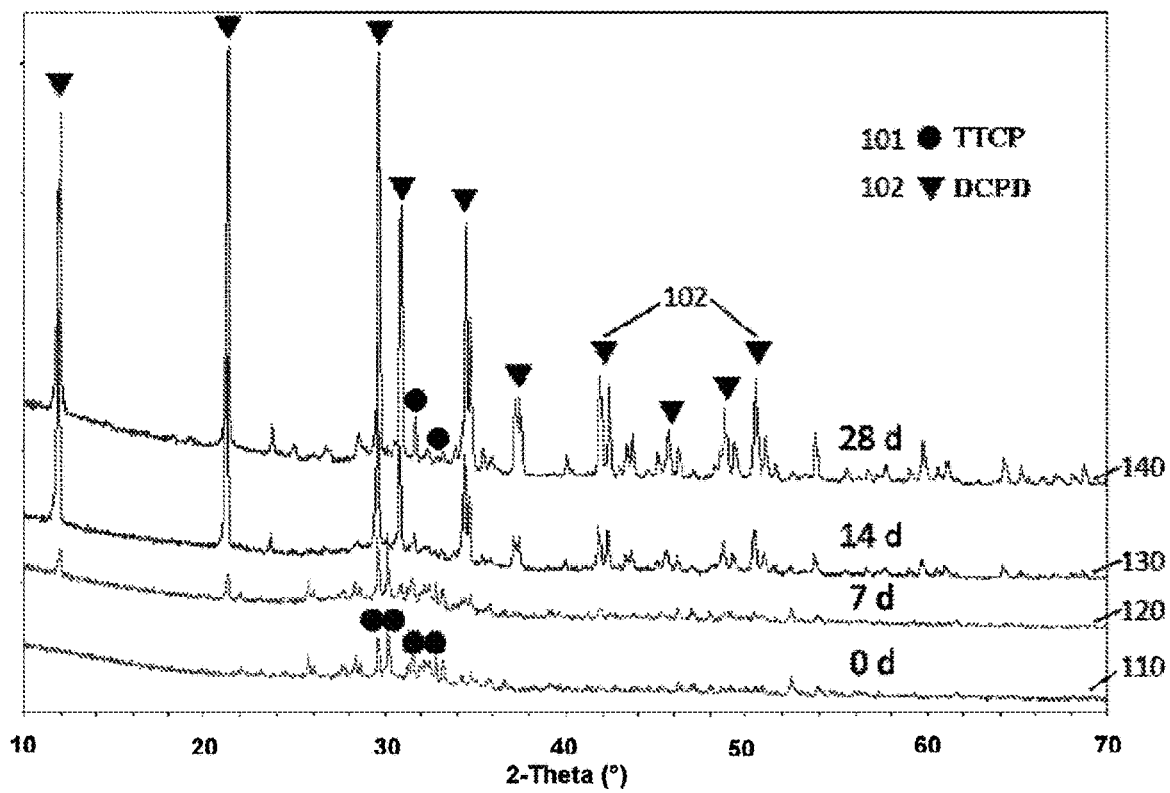
FIG. 1A is an X-ray diffraction (XRD) characterization of crystallization of an amorphous calcium polyphosphate (ACPP)/tetracalcium phosphate (TTCP), or ACPP/TTCP, cement according to one aspect of the present invention, the ACPP/TTCP cement having an ACPP:TTCP ratio of 1:0.225, after 4 weeks' incubation for confirmation the final product DCPD and the gradual conversion thereto.

The invention will now be described with reference to the accompanying drawings. Although this invention has been particularly shown and described with reference to preferred embodiments thereof, it will be understood by those skilled in the art that various changes in form and details may be made therein without departing from the scope of the invention encompassed by the appended claims.

As used herein, the term "ceramic" refers to an inorganic solid material including at least one of a metal, a nonmetal, and a metalloid atom, primarily held together by ionic and/or covalent bonds.

As used herein, the term "inorganic powder material" means a powder of an inorganic or ceramic material such as for example calcium polyphosphate.

As used herein, the term "about," means "approximately but not necessarily equal to," and when used in the context of a numerical value or range set forth means a variation of ±15%, or less, of the numerical value. For example, a value differing by ±15%, ±14%, ±10%, or ±5%, among others, would satisfy the definition of "about."

As used herein, the term "final products," may include composite, monolithic, or blended materials, including but not limited to any calcium-phosphate materials, for example dicalcium phosphate or hydroxyapatite.

As used herein, the term "polyphosphate" refers to a polymeric anion formed from at least two tetrahedral phosphate structural units linked together via sharing of an oxygen atom.

As used herein, the term "source" means a composition of matter containing the element or compound in any form. Thus, a calcium source contains the element calcium, and a phosphate source contains the compound phosphate.

This invention is directed to compositions of matter and methods for preparing bone cements from polyphosphate compounds and calcium and phosphate sources. In one aspect, the invention comprises a method of making a composite material from amorphous polyphosphate salts and calcium phosphate ceramics. Aspects of the invention include but are not limited to compositions of amorphous polyphosphate salts with calcium phosphate; preparation of amorphous polyphosphate salts granules or powders with controllable size and shape; preparation of calcium phosphate granules or powders with controllable size and shape; forms of powder/liquid pre-phase; and converted final products of the mixture after setting.

In one embodiment, an injectable bone cement is made comprising a first polyphosphate compound, and a second compound comprising calcium and phosphate. The first polyphosphate compound may comprise at least one polyphosphate salt. The first polyphosphate compound may comprise at least one of sodium polyphosphate, potassium polyphosphate, calcium polyphosphate, strontium polyphosphate, magnesium polyphosphate, aluminum polyphosphate, zinc polyphosphate, copper polyphosphate, cadmium polyphosphate, manganese polyphosphate, ammonium polyphosphate, and a chelated polyphosphate including composites and blends thereof. In one embodiment, the first polyphosphate is not sodium polyphosphate. In another embodiment, the second compound provides a phosphate which is a monomeric phosphate. In another embodiment, the second compound provides a phosphate which is not a polyphosphate.

The first polyphosphate compound may have a polyphosphate degree of polymerization of about 2 to about 10,000, or about 2 to about 9,000, or about 2 to about 8,000, or about 2 to about 7,500, or about 2 to about 7,000, or about 2 to about 6,000, or about 2 to about 5,000, or about 2 to about 4,000, or about 3 to about 3,000, or about 4 to about 2,500, or about 5 to about 2,200, or about 5 to about 2,000, or about 10 to about 1,800, or about 10 to about 1,750, or about 15 to about 1,600, or about 15 to about 1,500, or about 20 to about 1,400, or about 20 to about 1,300, or about 25 to about 1,200, or about 25 to about 1,000, or about 30 to about 900, or about 30 to about 800, or about 30 to about 700, or about 30 to about 600, or about 35 to about 500, or about 35 to about 400, or about 40 to about 350, or about 45 to about 300, or about 50 to about 250, or about 50 to about 200, or about 50 to about 150, or about 50 to about 125, or about 50 to about 100, or about 25 to about 75, or about 10 to about 220, or about 20 to about 100, or about 20 to about 200, or about 25 to about 500, or about 24. In certain embodiments, the degree of polymerization may be greater than 10,000, such as up to about 12,000, or up to about 15,000, or up to about 20,000, or up to about 50,000, or up to about 100,000, or up to about 500,000, or up to about 1,000,000. In another embodiment, the degree of polymerization of the polyphosphate is at least about 2. The injectable bone cement may have a polyphosphate compound with a particle size of about 1 nm to about 1 mm. The first polyphosphate compound may have a particle shape comprising any of circular, rectangular, cubic, pentagonal, hexagonal, needle-shaped, and fibrous-shaped.

The second compound may comprise a calcium phosphate ceramic. The second compound may comprise at least one of an amorphous calcium phosphate ceramic, an α-type calcium phosphate ceramic, an β-type calcium phosphate ceramic, and a gamma-type calcium phosphate ceramic. The second compound may comprise at least one of hydroxyapatite, calcium polyphosphate, octacalcium phosphate, tricalcium phosphate, amorphous calcium phosphate, monocalcium phosphate monohydrate, anhydrous monocalcium phosphate, dicalcium phosphate dihydrate (brushite), anhydrous dicalcium phosphate (monetite), and tetracalcium phosphate. In one embodiment, the second compound is not a polyphosphate compound. In another embodiment, the second compound is not a calcium polyphosphate.

In a particular embodiment, a polyphosphate hydrogel such as a CPP gel may be prepared by using amorphous CPP frits produced by pre-calcining calcium phosphate monobasic monohydrate ($Ca[H_2PO_4]_2:H_2O$) followed by rapid quenching in de-ionized distilled water. CPP frits are ground using a high-speed ball mill (Fritsch Planetary Micro Mill) and then passed through a sieve. CPP gel was prepared by mixing the CPP powder with distilled $H_2O$ and stirring at room temperature for a stirring time. The CPP slurry mixture was allowed to stand overnight for gel formation (or gelation). The second calcium and phosphate-containing compound was a calcium phosphate (CaP), which was prepared by solid-state reaction of dicalcium phosphate anhydrous (DCPA, $CaHPO_4$) and calcium carbonate ($CaCO_3$). The purity and particle size of CaP powder were characterized by SEM. The cement was prepared by mixing of CPP gel with the as-prepared CaP.

In one embodiment, a polyphosphate hydrogel such as a CPP gel may be prepared by using amorphous CPP frits produced by pre-calcining calcium phosphate monobasic monohydrate ($Ca[H_2PO_4]_2:H_2O$) at about 200 to about 600° C. for about 1 hour to about 100 hours before heating to about 1100° C. to about 1400° C. for about 0.5 hour to about 5 hour, followed by rapid quenching in de-ionized distilled water at room temperature. CPP frits were ground using a high-speed ball mill (Fritsch Planetary Micro Mill) and then passed through about 5 μm to about 300 μm sieve (Laboratory Test Sieves, Fisher Scientific). CPP gel was prepared by mixing the CPP powder with distilled $H_2O$ (about 0.01 gram/mL to about 0.2 gram/mL) and stirring for about 0.5 hour to about 4 hours. The CPP slurry mixture was allowed to stand for about 12 hours to about 96 hours for gel formation (or gelation). The second calcium and phosphate-containing compound was tetracalcium phosphate (TTCP) powder, which was prepared by solid-state reaction of dicalcium phosphate anhydrous (DCPA, $CaHPO_4$) and calcium carbonate ($CaCO_3$) (1:1 equimolar amount with a Ca/P ratio of 2) by heating at about 1500° C. for about 18 hours. The purity and particle size of TTCP powder were characterized by SEM (5-75 μm, mean 10±2.5 μm). The cement was prepared by mixing of CPP gel with TTCP (about 1:0.1 weight/weight ratio to about 1:10 weight/weight ratio).

It is to be noted that a polyphosphate compound, regardless of how the polyphosphate compound is prepared, is envisioned as being suitable for making a cement according to the principles of the present disclosure. This includes cements containing calcium polyphosphates, including amorphous calcium polyphosphate.

The polyphosphate compound have a gelation temperature of about 0 degrees Celsius to about 374.5 degrees Celsius, or from about 0 degrees Celsius to about 80 degrees Celsius, or from about 10 degrees Celsius to about 75 degrees Celsius, and a gelation time of about 1 minute to about 200 hours. Such range of gelation temperatures may also apply to nascent bone cement compositions just after mixing of the polyphosphate component with the calcium and phosphate source as well.

In one non-limiting embodiment, studies of the final product of the reaction of amorphous polyphosphate salts with calcium phosphate compounds demonstrate that a fast setting cement is formed, and that such cement is converted to a different form of calcium phosphate from the starting materials (i.e. dicalcium phosphate dihydrate (DCPD), dicalcium phosphate anhydrate (DCPA), or hydroxyapatite (HA) may be formed).

The formation of DCPD cement by the reaction of polyphosphate salts with alkali is one possible mechanism of action for a cement according to the present disclosure. However, the general reaction scheme may from another type of bone cement, such as hydroxyapatite type cement, or a DCPA (dicalcium phosphate anhydrate) cement. Without wishing to be bound by any particular theory, one factor which may determine the nature of the cement type is the ratio of ACPP/TTCP. With the increase of the TTCP (and thus the Ca/P ratio), the setting pH may be increased such that it may provide a favorable environment for the formation of a hydroxyapatite cement.

In another embodiment, a polyphosphate and tetracalcium phosphate are combined to form an injectable cement. In one embodiment, the polyphosphate may be calcium polyphosphate, particularly amorphous calcium polyphosphate (ACPP). ACPP is an acidic phosphate, and TTCP is an alkali phosphate. The resultant mixture is an injectable, shapable, highly viscous, bone graft scaffold for both bone and soft tissue engineering. This injectable cement can be used as a bone void filler and controllable and sustained drug release tool to further enhance porous inorganic (ceramic) structures in monolithic form or for use as a porous structure for infiltration with an appropriate organic polymer to form novel interpenetrating ceramic/polymer composites, and in particular a method of manufacturing such structures. The final conversion product is biocompatible and biodegradable mineral that can firmly integrate to surrounding bone tissue and enhance osteogenesis.

The cements can be used as a matrix for mixing different materials, including but not limited to inorganic chemicals and compounds, organic molecules, polymers, and biological molecules such as amino acids, nucleotides, nucleic acids, enzymes and other proteins, and cultured cells.

The cement is formed using a first starting material formed of at least one inorganic polyphosphate in hydrogel form. The hydrogel has a low ratio of calcium:phosphate, between about 0.50 and about 0.95, or about 0.50 and about 0.90, or about 0.50 and about 0.85, or about 0.50 and about 0.75, or about 0.5. The hydrogel is reacted with a second calcium phosphate composition having a higher calcium:phosphate ratio, about 1.15 to about 3.00, or about 1.25 to about 2.75, or about 1.50 to about 2.50, or about 1.75 to about 2.25, or about 2.00. The reaction converts the materials to a new product with a new calcium:phosphate ratio between the higher ratio and the lower ratio. The final calcium:phosphate ratio can be about 0.5 to about 2.0.

In one aspect, a long polyphosphate chain is chelated with multiple calcium phosphate monomers or other small molecules from materials listed above.

In one embodiment of the present invention, with the modification of various parameters, a polyphosphate cement (PPC) can be formulated to a desired mechanical strength and pore size range suitable for a particular application. The speed at which final products are generated can also be altered.

PPC can be used in combination with other bone ceramics and with bioactive glass, or with combinations of these types of materials. Such materials include but are not limited to hydroxyapatite, tricalcium polyphosphate, calcium sulfate, calcium carbonate, calcium chloride, and so forth. Moreover, the shape of ACPP and TTCP powder can be spherical, fibrous or irregular. And the crystal structure of ACPP and TTCP can be single crystal, poly-crystal, semi-crystal or amorphous. The formed composites can be used as a new bone-like bone graft substitute, which is of higher viscoelasticity, higher adhesion, desired pore size, good biocompatibility, highly adjustable mechanical strength (from about 25 megapascal (MPa) to about 1 GPa, or from about 25 MPa to about 500 MPa, or from about 25 MPa to about 250 MPa, or from about 25 MPa to about 200 MPa, or from about 25 MPa to about 150 MPa, or from about 25 MPa to about 100 MPa, or from about 30 MPa to about 90 MPa, or from about 35 MPa to about 85 MPa, or from about 40 MPa to about 80 MPa, or from about 40 MPa to about 75 MPa, or from about 50 MPa to about 75 MPa, or from about 50 MPa to about 70 MPa, or from about 55 MPa to about 70 MPa, or from about 60 MPa to about 70 MPa, or about 50 MPa, or about 55 MPa, or about 60 MPa, or about 65 MPa, or about 70 MPa). By contrast, existing CPCs such as Hydroset CPC only have compressive strength in the range from about 5 MPa to about 20 MPa. In another embodiment, the compressive strength of a polyphosphate-based cement can be tuned to be similar to that of a cement for non-load bearing applications. For instance, the compressive strength of the polyphosphate-based cement can be between about 2 MPa to about 250 MPa, or about 5 MPa to about 250 MPa, or about 5 MPa to about 200 MPa, or about 5 MPa to about 150 MPa, or about 10 MPa to about 100 MPa, or about 5 MPa to about 25 MPa, or about 5 MPa to about 20 MPa. The biodegradation time of a PPC can also be highly tuned (days to months; for example, from about 1 day to about 365 days, or about 2 days to about 350 days, or about 5 days to about 300 days, or about 14 days to about 280 days, or about 21 days to about 240 days, or about 28 days to about 200 days, or about 35 days to about 160 days, or about 42 days to about 120 days, or about 49 days to about 98 days, or any range from a minimum of between about 1 day to about 364 days, to a maximum of about 2 days to about 365 days, or any duration therebetween). These injectable ACPP/TTCP grafts can be easily delivered to the lesion site through a regular syringe, pipet, or injection gun, including by hand by a healthcare professional, which is an advantage conferred by the fact that the bone-filling gel is shapeable and flexible.

In another aspect, the invention relates to a combined use of CPP gel as a targeted and local drug and stem cell delivery tool. Molecules or cells of interest can be soaked into the gel matrix and the complex can be introduced to a site in or on a body, resulting in the delivery of the material of interest. The types of compounds which can be introduced include but are not limited to: antibiotics, such as those selected from the families of minoglycosides, ansamycins, carbapenems, cephalosporins, glycopeptides, lincosamides, lipopeptides, macrolides, penicillins, tetracyclines, and others; growth factors, such as angiopoietin (Ang), bone morphogenetic proteins (BMPs), erythropoietin (EPO), fibroblast growth factor (FGF), growth differentiation factor-9 (GDF9), insulin-like growth factor (IGF), nerve growth factor (NGF) and other neurotrophins, platelet-derived growth factor (PDGF), transforming growth factor alpha (TGF-α), transforming growth factor beta(TGF-β), vascular endothelial growth factor (VEGF), placental growth factor (PlGF), and others; and compounds of another pharmaceutical genus.

Furthermore, cells can be soaked into the matrix and delivered to the site of interest. Cell types could be any type of cell or cells from humans or animals. They can be either well-differentiated cells (from commercially-available cell lines or isolated from animal or human tissues) or stem cells found in any multicellular organism that can divide (through mitosis) and differentiate into diverse specialized cell types and can self-renew to produce more stem cells. The stem cells can either be embryonic stem cells or adult stem cells, which are found in various tissues.

One aspect of this invention is the mechanism acting during CPP gelation and the effects of amorphous CPP length and the size or shape of particles on the physiochemical properties of a CPP gel. Use of this property has resulted in the design of calcinations and grinding procedures that lead to the reliable formation of injectable CPP scaffolds. Descriptions of calcium phosphates suitable for use in accordance with the principles of the present invention can be found in International Patent Application PCT/US14/45423, the entire contents of which are incorporated herein by reference.

Prior to being gelated, the polyphosphate compound, such as ACPP, may be provided as salt granules or powders with controllable size and shape. The particles may have an average size in a range from a maximum dimension of about 1 nanometer to about 1000 micrometers, or about 5 nanometers to about 800 micrometers, or about 10 nanometers to about 500 micrometers, or about 25 nanometers to about 250 micrometers, or about 50 nanometers to about 100 micrometers, or about 100 nanometers to about 50 micrometers, or about 200 nanometers to about 25 micrometers, or about 250 nanometers to about 10 micrometers, or about 500 nanometers to about 5 micrometers, or about 1 micrometer to about 5 micrometers, or about 1 nanometer to about 10 nanometers, or about 1 nanometer to about 100 nanometers, or about 1 nanometer to about 1 micrometer, or about 1 nanometer to about 10 micrometers, or about 1 nanometer to about 100 micrometers, or about 1 nanometer to about 200 micrometers, or about 1 nanometer to about 500 micrometers, or about 10 nanometers to about 100 nanometers, or about 100 nanometers to about 1 micrometer, or about 1 micrometer to about 10 micrometers, or about 10 micrometers to about 100 micrometers, or about 100 micrometers to about 1000 micrometers, or any range having endpoints in the range from about 1 nanometer to about 1 millimeter. In some embodiments, the particle size may be selected based on the clinical application for which the cement is to be used. The polyphosphate particles can have a particle shape comprising any of circular, rectangular, cubic, pentagonal, hexagonal, needle-shaped, and fibrous-shaped, or any combination thereof.

Inorganic fillers can be incorporated into the inventive cement. The inorganic filler may comprise at least one of a bioglass, a silica ceramic, an oxide ceramic, a carbon fiber, a metal, and a metal alloy. The inorganic filler may comprise a powder having a particle size of about 1 nanometer to about 1000 micrometers. The inorganic filler can have a particle shape comprising any of circular, rectangular, cubic, pentagonal, hexagonal, needle-shaped, and fibrous-shaped Organic fillers can be incorporated into the inventive cement. The organic filler can have a particle size of about 1 nm to about 1 mm. The organic filler can have a particle shape comprising any of circular, rectangular, cubic, pentagonal, hexagonal, needle-shaped, and fibrous-shaped. The organic filler can be both in powder and liquid form.

An organic filter can comprise at least one of a polycarboxylate, a polysulfate, polysulfonates, a polyphosphate, a polyamine, a polyurea, a polyamide, a polyalkylene oxide diol, a polyalkylene oxide diamine, a polycarbonate, a polylactone, a polyethersulfone, a polyvinyl, a polypeptide, a polysaccharide, a polyurethane, a polysulfone, a polycarbonate, a polyester, polyethylene, polypropylene, polystyrene, polysilicone, poly(acrylonitrile-butadienestyrene), polybutadiene, polyisoprene, polymethylmethacrylate, polyvinylacetate, polyacrylonitrile, polyvinyl chloride, polyethylene terephtalate, cellulose, a polysilicone, a polyolefin, a polyvinyl derivative, a polypeptide derivative, poly(lactic-co-glycolic acid), and a polysaccharide derivative. The organic filler can comprise a carboxylate, a sulfate, a sulfonate, a phosphate, an amine, urea, an amide, an alkylene oxide diol, an alkylene oxide diamine, a carbonate, a lactone, an ethersulfone, a vinyl, a peptide, a dimethacrylate, a saccharide, a urethane, a sulfone, an ester, an ethylene, propylene, a styrene, silicone, acrylonitrile-butadienestyrene, butadiene, an isoprene, methylmethacrylate, vinylacetate, acrylonitrile, vinyl chloride, ethylene terephtalate, an olefin, a vinyl derivative, bisphenol A, a bisphenol A derviative, an oligosaccharide, a peptide derivative, lactic acid, glycolic acid, cyanoacrylate, a cyanoacrylate derivative, and a saccharide derivative.

In one non-limiting embodiment, a cement was made from ACPP and TTCP, and characterized using scanning electron microscopy (SEM). The morphology of the solidified CPP gel surface was characterized by SEM (JSM-6510LV-LGS, MA, USA). The solidified CPP gel was coated with gold (Gold Sputter, Effa Coater, USA) before SEM analysis. Morphologies were viewed at about 25 kV accelerating voltage.

Figure 1B:
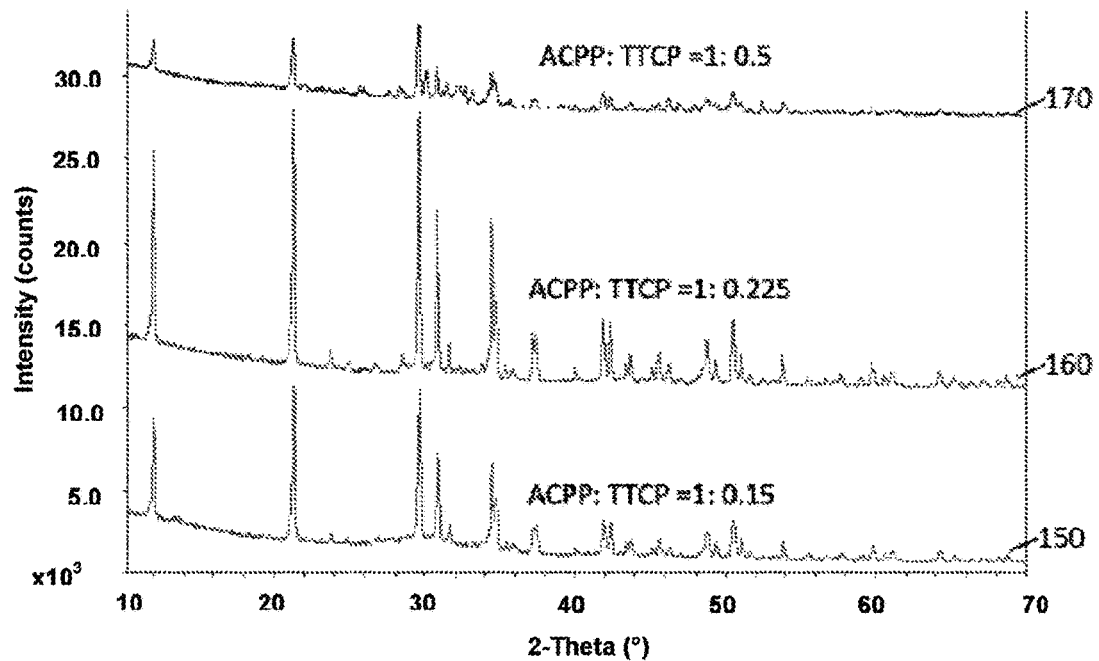
FIG. 1B is an XRD analysis of final product ACPP/TTCP cements in accordance with one aspect of the present invention with different ACPP/TTCP ratios (ACPP:TTCP=1:0.15; 1:0.225; and 1:0.5) after 4 weeks' incubation.

Turning now to FIG. 1A and FIG. 1B, the invention as disclosed herein can be characterized using X-ray diffractometry (XRD). The crystalline structures of CPP after gelation were characterized using an X-ray diffractometer (Rigaku SmartLab, Woodlands, Tex.). CuKα radiation ($\lambda=1.5418$ A) was used to scan the diffraction angles ($2\theta$) between about 10° and about 80° at a speed of about 5°/minute. The spectra were compared with standard spectra from the JCPDS card via Jade 5 software in order to identify the sample phases and crystalline structures. The XRD result shows a gradual phase conversion from ACPP/TTCP mixture to DCPD during incubation at 37° C. and 95% humidity. As shown in FIG. 1A, the characteristic peaks of spectrum at 0 days (plot 110) and 7 days (plot 120) after mixing of the cement are correlated with TTCP from JCPDS standard PDF card 25-1137; TTCP peaks are indicated with circles 101. At the 0 days time point (110), the crystalline phase was identified as TTCP when compared to standard JCPDS card, while the ACPP phase was not shown due to the amorphous nature. After 7 days incubation (120), the main crystalline phase remains TTCP. However, some characteristic peaks of DCPD emerged at 12 and 21. The characteristic peaks of the spectrum after 14 days (plot 130) are correlated with DCPD from JCPDS standard PDF card 72-0713; DCPD peaks are indicated by triangles 102. At 14 d, the twin peaks of TTCP at around 30 were converted to single sharp peak, and most DCPD peaks were shown around 40-50. At 28 d, DCPD peaks kept growing. And the TTCP peaks around 31 were still shown, which indicates the existence of remaining TTCP phase.

The twin peaks at around 30 and finger peaks at 31-32 were assigned to be the characteristic peaks of TTCP, and the sharp peaks at 12, 21, 30, 35, 37 and 50 were assigned to be the charaterstics of DCPD. After 28 days (plot 140), the DCPD peaks are even more pronounced, indicating continued conversion of the cement after mixing and setting. Taken together, these results show that the cement undergoes recrystallization after injection and setting, and gradually converts to DCPD (FIG. 1A).

As shown in FIG. 1B, ACPP/TTCP cements with varying ACPP/TTCP proportions (including but not limited to ACPP:TTCP=1:0.15, plot 150; 1:0.225, plot 160; and 1:0.5, plot 170) exhibit a similar phase conversion trend that indicates crystallinity change over time. The initial crystallinity is calculated from the TTCP compartment as higher TTCP proportion with higher crystallinity. At 7 days after mixing, the crystallinity drop may be due to the initiation of conversion of ACPP/TTCP to DCPD. Followed by the recrystallization, the crystallinity of cement has increased to a similar level at 28 days after mixing.

Rheological data pertaining to CPP gels were also obtained. An ARG2 rheometer with standard parallel-plate geometry of 20 mm diameter was used for rheological characterization of CPP gels. 1 ml of each sample was placed on the rheometer. The experiments were performed under a closed environment via the equipped solvent trap system to eliminate solvent loss. A non-oscillatory stress sweep (stress amplitude from about 0.001 pascal to about 1 pascal) at fixed frequency (about 0.16 hertz) was applied to the sample to determine the pseudo-linear viscolelastic region (LVR) with data collected at ten points per decade. An oscillation time sweep was also performed to confirm the properties of the material did not change over time. Storage modulus (G'), loss modulus (G"), and complex viscosity ($\eta^*$) were measured. Steady-state flow (shear rate amplitude from about 0.001 to about 100 pascal was applied to the sample to determine the dynamic viscosity of the samples. The measurements were performed at about 25 degrees Celsius to obtain the dynamic viscosity. Finally, a creep-recovery experiment with fixed stress and time values was performed using the data collected in previous experiments. In order to investigate the setting property of CPP gel, an oscillatory time sweep was applied at fixed stress and frequency to the sample with the solvent trap released. The sudden elevation and disorder of G' and G" was recorded as confirmation of the setting point. CPP gel was also measured seven days post-mixing to investigate change in the rheological properties. Similar measurements were performed (oscillation stress sweep, frequency sweep, time sweep, static state flow, and creep recovery.)

Creep recovery data shows that one hour after mixing, a calcium polyphosphate will interact with water, but has not yet formed much of a network structure. However, seven days after mixing and the gel being kept at room temperature, the recovery is about 70%, indicating the formation of the network, potentially by entanglement of polyphosphate chains.

As for the viscoelastic properties of a calcium polyphosphate gel, CPP gel displays a viscous fluid property with higher loss modulus G" and complex viscosity around 1 Pa*S, indicating a sol-gel interaction to some extent. Oscillatory frequency sweet tests demonstrate a typical Maxwell-type behavior where G' dominates and G'/G" is slight. Such properties contribute to the injectability of the hydrogel.

The viscosity of polyphosphate gels, particularly calcium polyphosphate gels, may be adjusted by the temperature at which they are prepared. The viscosity of CPP gels prepared at about 90 degrees Celsius are lower, at about 3 Pa*S, than those prepared at room temperature, at about 5-6 Pa*S. The reduced viscosity due to heating might be caused by the breakdown of the bonding of the intermolecular polyphosphate chains and the reduction of the chain entanglements during heating. A longer soaking time with stirring also reduces viscosity of a CPP gel. Minor stirring of the hydrogel (about 15 minutes) produces the highest degree of creep recovery. Viscosity is also impacted by the CPP particle size; CPP gel with larger particles (average size of greater than about 75 microns) when compared to those of smaller size (average particle size of less than about 75 microns). Additionally, viscosity of a polyphosphate hydrogel is impacted by stirring time. Among CPP hydrogels prepared at room temperature, viscosities range from about 6 Pa*S to about 100 Pa*S. Viscosity of a CPP hydrogel increases as stirring time increases from 0 to about 90 minutes, and gradually decreases with additional stirring. At a time of about 240 minutes of stirring, a CPP hydrogel loses its viscosity and transforms to a stable liquid. At about 90 minutes of stirring, a CPP gel shows the highest G'/G" ratio, indicating the staging for most colloid formation. CPP gelation continues even beyond the ending of stirring, and the structure of CPP gel is stable even when stored in a −20° C. freezer. The polyphosphate/calcium/phosphate cements of the present invention, in particular embodiments combining ACPP and TTCP, have initial viscosities in the range from about 6 Pa*S to about 100 Pa*S, a range which represents good flowability for the ACPP gel. The initial viscosity can also range from about 10 Pa*S to about 80 Pa*S, or about 15 Pa*S to about 75 Pa*S, or about 20 Pa*S to about 70 Pa*S, or about 25 Pa*S to about 65 Pa*S, or about 30 Pa*S to about 60 Pa*S, or about 35 Pa*S to about 55 Pa*S, or about 35 Pa*S to about 50 Pa*S, or about 10 Pa*S to about 50 Pa*S.

Figure 2:
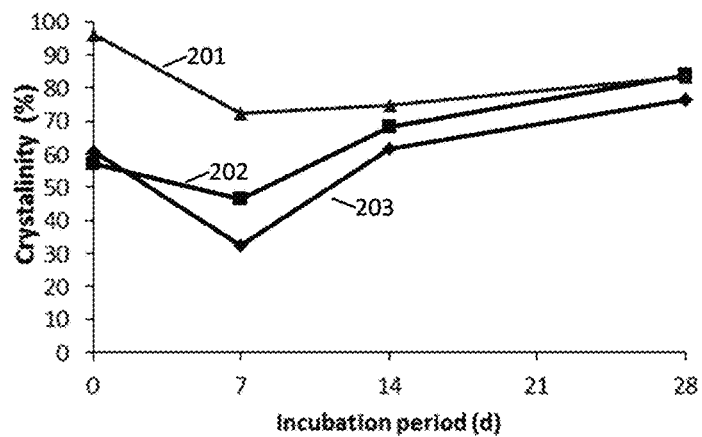
FIG. 2 is a graphical representation of percent crystallinity change of a variety of ACPP/TTCP cements as measured at different times during incubation; the ACPP:TTCP ratios are: plot #2=1:0.15; #3=1:0.225; #4=1:0.5.

The conversion of ACPP/TTCP cement over time is illustrated in FIG. 2. The recrystallization of cement is achieved by mixing TTCP powder and ACPP gel (both consisting of particle size less than 75 μm), in ACPP/TTCP ratio at 1:0.15 (plot 203), 1:0.225 (plot 202), 1:0.5 (plot 201). A transient reduction of the crystallinity was found in all formulations and it was due to the conversion of TTCP to amorphous metaphase. After transition, the crystallinity as shown in plot 203 comes from newly formed DCPD crystals, while most crystallinity of the 1:0.5 ratio mixture (plot 201) comes from unconverted TTCP. The result shows that the higher amount of $PO_4$ provided by ACPP, the higher the efficiency of DCPD conversion from TTCP in the composite may be. In one embodiment, the period after 14 days is the period of DCPD crystal growth.

As shown in FIG. 3A-3D, a polyphosphate/calcium phosphate cement as disclosed herein is characterized using $^{31}P$-solid-state NMR. Single pulse excitation experiments were performed on as-made amorphous ACPP, ACPP-TTCP mixture powder, TTCP, DCPD powder by $^{31}P$ MAS Solid State NMR using a Bruker Avance spectrometer (about 400 MHz, about 9.4 T, 4 mm rotor) having a spinning rate of about 10000 Hz. The integrated peak areas (%) for each phosphorus species (Q0, Q1, Q2) present were subsequently used to calculate the average phosphate chain length (CL) using the following equation: CL=2(Q1+Q2)/Q1.

Figures 3A, 3B, 3C, 3D:
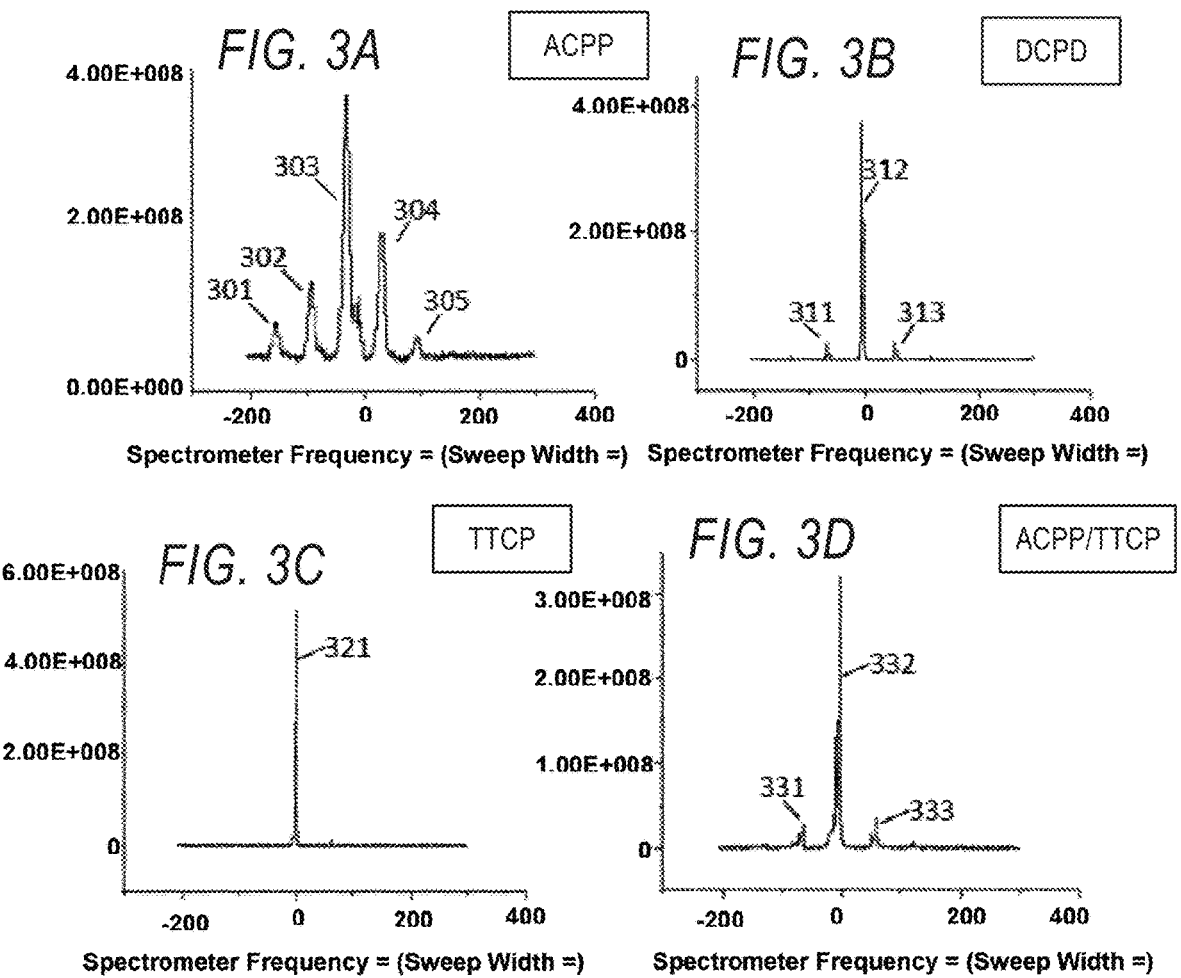
FIG. 3 is magnetic angle spinning nuclear magnetic resonance (MAS-NMR) characterizations of ACPP, dicalcium phosphate dihydrate (DCPD), TTCP, and ACPP-TTCP (after incubation for 4 weeks) making use of the 31P isotope.

The components or putative components of a cement of the present disclosure were investigated in FIGS. 3A-3C. For ACPP, the characteristic spectrum (FIG. 3A) shows a peak at −31.2 ppm (peak 303) which is a characteristic of middle phosphate groups. The shoulder peaks around −8, −15 and −20 ppm (Q1, to the right of 303) are characteristic of end phosphate groups. All other peaks (301, 302, 304, 305) are from spinning side-bands of Q2. The presence of Q1 and Q2 units in solid-state NMR result of ACPP demonstrates the presence of long phosphate chains (Q2 middle groups with Q1 end groups). According to the equation in materials and methods, calculated CL is 24.8, which indicates an average of 24.8 repeating phosphate units in ACPP linear structure. DCPD (FIG. 3B) and TTCP (FIG. 3C) show a similar curve with one major peak (312, 321) and two tiny spinning side bonds (311 and 313, as best seen in FIG. 3B.) The dominant singular peak around −8 ppm demonstrates the presence of all end phosphate groups (Q1) in DCPD and TTCP. An ACPP/TTCP combination cement, as illustrated in FIG. 3D, shows the presence of a substantial number of end groups (peak 332) but also a number of end groups (peaks 331 and 333).

Figure 4:
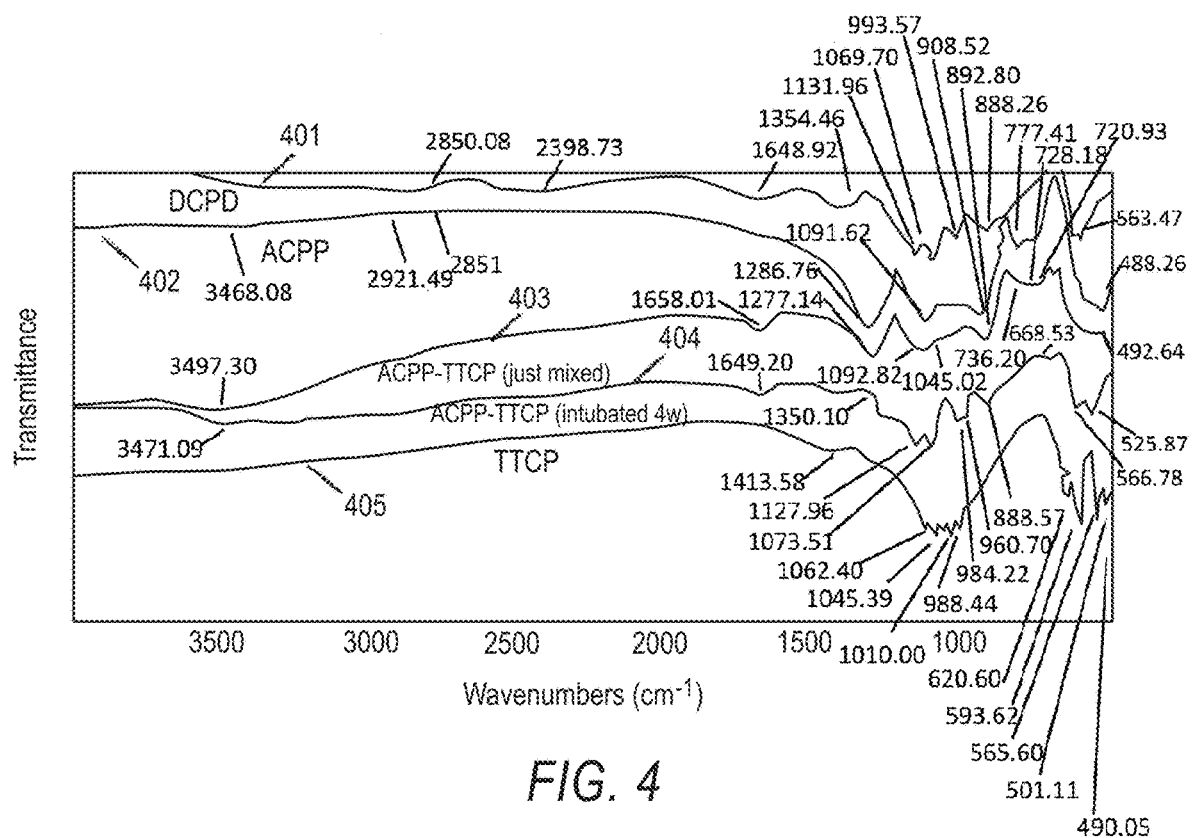
FIG. 4 is a Fourier transform infrared spectroscopy (FTIR) characterization of ACPP, DCPD, TTCP, ACPP-TTCP (0 day time point, just mixed) and ACPP-TTCP (28 days after incubation)

The invention disclosed herein can be characterized using Infrared spectroscopic measurement. As illustrated in FIG. 4, Fourier transformed infrared (FTIR) spectral analysis was carried out on a Paragon 500 FTIR Spectrophotometer (Perkin-Elmer). A series of scans were run from wavenumbers about 4000 to about 400 $cm^{-1}$, at an interval of about 2 $cm^{-1}$ and with a resolution of about 1 $cm^{-1}$. Sample pellets were made by drying and pressing with KBr and ground scaffold powder (ACPP, plot 402; DCPD, plot 401; TTCP, plot 405; and ACPP-TTCP, just after mixing in plot 403, and after four weeks' incubation, plot 404). For DCPD (401), the characteristic sharp peaks and trough assignments are 1650 $cm^{-1}$ (O—H stretch), 1131 $cm^{-1}$ and 993 $cm^{-1}$ (P—O stretch), 1070 $cm^{-1}$ (P—O stretch loss) and 888 $cm^{-1}$ (P—OH). These are consistent with a brushite (dicalcium phosphate dihydrate, DCPD) standard. For TTCP (405), the finger peaks around 1062 and 1010 $cm^{-1}$ were attributed to v3-P—O vibrations of phosphate groups ($PO_4^{3-}$); the absorption peaks at 620 and 565 $cm^{-1}$ corresponded to v4-P—O vibrations of $PO_4^{3-}$ besides of the above described absorption peaks, respectively. For ACPP (402), FTIR shows the broad peaks at 720-780 and 850-920 $cm^{-1}$ (vibration bands of a linear P—O—P bond) and an O—P=O bond at 1200-1360 $cm^{-1}$, respectively. These demonstrate that the synthesized powder is amorphous CPP. For ACPP-TTCP (just mixed) (403), the spectrum is consistent with the ACPP spectrum, which indicates the initial ACPP-TTCP mixture is ACPP dominant in content. However, For ACPP-TTCP (incubated for 4 week) (404), the spectrum shows a transition to DCPD with characteristic peaks at 1650 $cm^{-1}$ (O—H stretch), 1128 $cm^{-1}$ and 984 $cm^{-1}$ (P—O stretch), 1074 $cm^{-1}$ (P—O stretch loss) and 888 $cm^{-1}$ (P—OH). This result also suggests a gradual transition of a ACPP/TTCP mixture to newly-produced DCPD after incubation at 37° C.

Turning now to FIGS. 5A-5D, calcium phosphate species, including those which correspond to an invention disclosed herein, were analyzed by scanning electron microscopy (SEM). The SEM morphological image of FIG. 5A shows the gradual conversion of the surface of a cement of the present disclosure from ACPP/TTCP to DCPD during incubation at 37° C. and 95% humidity for 28 days. The formation of new DCPD crystals is shown as monoclinic rod-shape (star, 502), and the underreacted TTCP with contacting water is shown as typical whisker-shape, indicated by arrows 501. DCPDs grow gradually to larger crystals from TTCP whiskers. The setting cement of the present disclosure contains an interlocked polycrystal structure. The formed DCPD crystal shows a monoclinic prismatic shape, which is comparable to DCPD standard. As shown in FIG. 5A, no obvious remaining TTCP crystal can be found, which also indicated the completion of DCPD transition at this stage. This result confirms the conclusion with XRD analysis. Under SEM, the cement is revealed to have a structure consisting of an ACPP and TTCP substrate integrated with scattered recrystallized DCPD granules (FIG. 5A). The post-setting ACPP/TTCP cement is a polycrystal composite. For reference, FIG. 5B shows an SEM micrograph of amorphous CPP, FIG. 5C shows TTCP, and FIG. 5D illustrates DCPD.

Figure 6A:
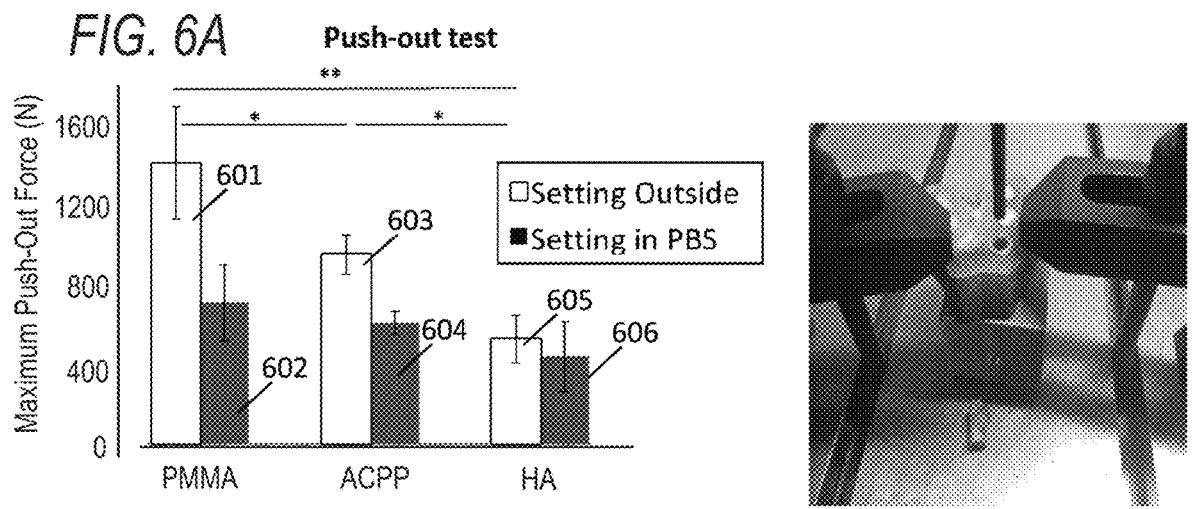
FIG. 6 is a graphical representation of the results of push-out test from ACPP/TTCP cement vs. poly(methylmethacrylate) (PMMA) cement vs. CPC cement in a porcine tibia defect model for demonstration of bonding strength.

As shown in FIG. 6A, a cement according to one embodiment of the present invention can be characterized using Infrared spectroscopic measurement ex-vivo push-out test. An ex-vivo porcine tibia bone defects pre-filled with PPC were used to evaluate the bonding strength between the implanted cements and surrounding bone tissues. The results of the amorphous CPP-based cement are shown in bars 603 and 604 of the graph. Bone defects pre-filled with Simplex® (PMMA cement, bars 601 and 602) and Hydroset® (CPC cement, bars 605 and 606) were included as controls for comparison. Each experiment was repeated three times and each setting included 3 samples. Bone cements were injected into the predrilled bone defects and allowed setting at both in dry (bars 601, 603, and 605) and wet (PBS, about 37 degrees Celsius; bars 602, 604, and 606) conditions.

Figure 6B:
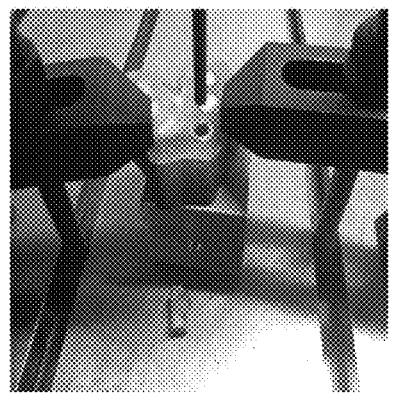

As shown in the photograph of FIG. 6B, the proximal plate parts (with implanted materials) of tibia samples were used for push-out testing. Soft tissues around the tibia were removed to expose the surface of the implants. The dorsal side of the tibia sample was then fixed. Approximate alignment was achieved by positioning the tibia parallel to push-out probe with the loading axis of the Instron model 8841 Universal Materials Test Machine. Proper specimen alignment was obtained by adjusting the two rotational axes of the fixture while using continuous fluoroscopy to confirm perpendicularity of the rods with respect to the fixture base. Once the fixture is attached to the load cell, the fixture aligned along the x-axis and y-axis cross slides to obtain alignment between the extraction materials of the implants. Under position control, the Instron 8841 actuator pushes the materials out at a rate of about 1 mm/minute. Actuator position and load were recorded using built-in software. The Ultimate Shear Strength (the peak push-out force) and energy for complete push out (integration of push out force and displacement) were used to measure the bonding strength.

Analysis of the results displayed in FIG. 6A, the ex-vivo porcine tibia model data demonstrate that the push-out force of an amorphous calcium polyphosphate-based cement ACPP, bar 603) is quite promising and significantly higher than conventional CPC hydroset cement, which indicates the better and stronger bonding strength of ACPP (bar 605) to surrounding bone tissue. One of the biggest limitations of CPC cement is its poor affinity and bonding strength to surrounding bone tissue, which cause earlier failure of implant. In other hand, PMMA has much higher mechanical strength (bar 601) compared to CPC and ACPP, but can have stiffness which is too high to bond with native bone, in turn causing a stress shielding effect. Therefore, providing a bone cement with an appropriate bonding strength and mechanical properties close to native bone is desirable. In the PBS soaking condition (bars 602, 604, and 606 of FIG. 6A), similar results have been presented. In these results, PPC shows higher bonding strength (about 600 Newtons, bar 604) compared to CPC (about 400 Newtons, bar 606), whereas the lower bonding strength of PPC (as compared to PMMA, about 700 Newtons) might be ideal to provide temporal support and promote native bone regeneration.

Figure 7A:
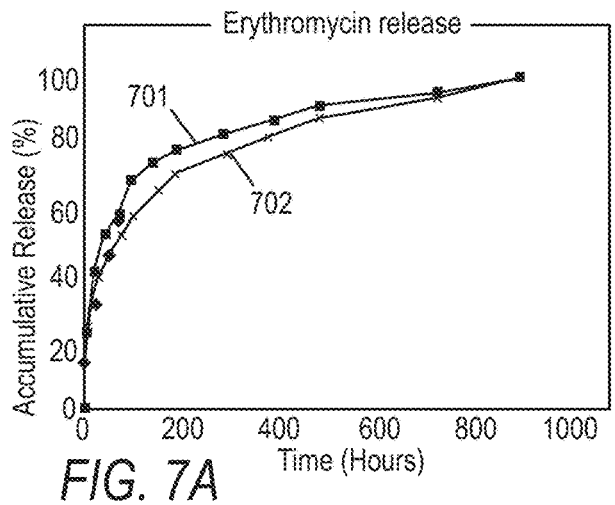
FIG. 7A is a graphical representation of incorporated erythromycin (EM) release profiles from an ACPP/TTCP cement in vitro in accordance with another aspect of this invention.
Figure 7B:
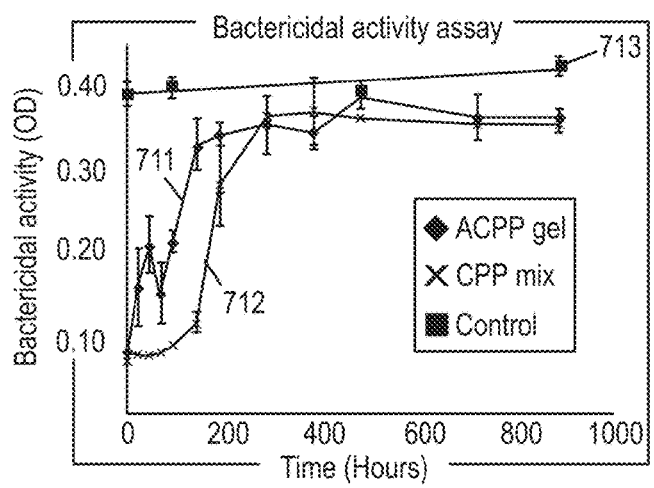
FIG. 7B is a graphical representation of the results of a bactericidal activity assay of released eluent collected from the study of FIG. 7A.

As illustrated in FIGS. 7A and 7B, the polyphosphate-containing cement according to some embodiments of the present invention may be impregnated with substances for delivery into the body. FIG. 7A shows a study of release of erythromycin (EM), a commonly used antibiotic, from CPP mix cement in vitro. Erythromycin release from CPP mix cement was analyzed by incubation of CPP cements in about 1 ml of $DH_2O$ in sealed polystyrene tubes (Corning, USA). Samples were continuously agitated in a water bath (about 36.5±about 0.5° C.). At each time point, aliquots of degraded simulated body fluid (SBF) medium were removed for measurement. Erythromycin released from each removed sample and was measured using an ultraviolet-visible spectrophotometer at OD 235 nm. About 100 μL collected medium was added to 100 μL prepared alkaline solution (about 0.12M, sodium phosphate; about 0.25M, sodium hydroxide) in about 60° C. water bath for about 15 minutes. After cooling to room temperature, reacted solution was then examined using a UV/VIS Spectrophotometer at wavelength of 235 nm. This wavelength was chosen because the large ring lactone of erythromycin can react with NaOH and the final product with C=O bond has maximum absorbency at wavelength of 235 nm. The standard OD-concentration curve (not shown) was drawn by measuring gradient erythromycin solutions. Thus, the erythromycin concentration in medium can be calculated from the standard equation by reading OD values.

FIG. 7A shows the drug loading and releasing capability of PPC cement after solidification. EM was mixed with ACPP before gel preparation and the final EM concentration in the CPP mix was 5% (w/w). The cumulative EM release from both ACPP/TTCP mixture (plot 702) and ACPP gel without incorporation of TTCP (plot 701) showed a similar pattern and lasted for up to about 900 hours (about 37.5 days). A sustained EM release observed is mainly due to the ionic binding of EM to the polyphosphate structure of ACPP gel. The inclusion of TTCP has little effects on this ionic binding. Different compositions of the cement, combined with different chemical characteristics of the compound to be released, will govern the amount of time it takes to release a particular compound.

To illustrate the efficacy of a drug after release from a CPP cement according to an embodiment of the present invention, FIG. 7B shows the results of studies of bactericidal activity of a drug secreted from a CPP cement. A modified minimum inhibitory concentration (MIC) assay was developed to measure the bactericidal activity of erythromycin eluted from the CPP mix cements. Briefly, a Mueller-Hinton broth inoculated with *S. aureus* spores was cultured at about 37° C. until an absorbance reading of about 0.08 to about 0.1 was attained at 625 nm, corresponding to roughly $1-2\times10^8$ CFU/ml. Then about 200 μl of eluents from CPP mix cements collected at various time points was added into about 800 μL of the bacterial broth and incubation continued at about 37° C. for about 6 hours, followed by OD measurement at about 625 nm. The MIC was determined by the lowest concentration that inhibited the growth of bacterium as characterized by a lack of turbidity and lower OD readings. Bacterial culture in Mueller Hinton broth without erythromycin was included as a positive control. Bactericidal activity assays were conducted in duplicate for both the blank and testing samples.

As shown in FIG. 7B, EM released from a polyphosphate cement is stable and active. CPP mix remained the bactericidal activity above MIC level for at least two weeks, and lasted for up to 40 days. The bactericidal activity of EM eluted from ACPP gel is somewhat weaker than that from ACPP/TTCP cement mixture. The reduced EM stability in ACPP gel might be due to its acidic environment (Ca:P ratio 0.5). A neutral pH of CPP mix can be reached by incorporation of TTCP (Ca:P ratio 2.0), which has been confirmed by our previous studies. About 30% of EM remained in the residue of ACPP/TTCP cement mixture after about 2 months in culture. EM release may be closely linked with the ACPP/TTCP mixture degradation rate. An initial burst of EM release (about 20% released within about 24 hours) provides an instant protection against bacterial adhesion and growth. Subsequently a controllable and sustained EM release was observed through a diffusion of EM from the slow-degrading ACPP/TTCP mixture, until release and degradation is completed.

FIG. 8 illustrates the results of atomic force microscopy (AFM) studies on the surface of a cement made in accordance with an embodiment of the present invention. The roughness of the surface was characterized using a Multi-mode IIIa AFM (Digital Instruments) and a Dimension 3100 AFM (VEECO). AFM imaging of the inventive polyphosphate cement was conducted using tapping mode in air. Positioning within micrometer accuracy of the cantilever on top of the discs is achieved by the integrated optical microscope. The data were collected by mapping the area within a 1.2×1.2 µm² sized grid to obtain both amplitude and phase images.

Figure 8A:
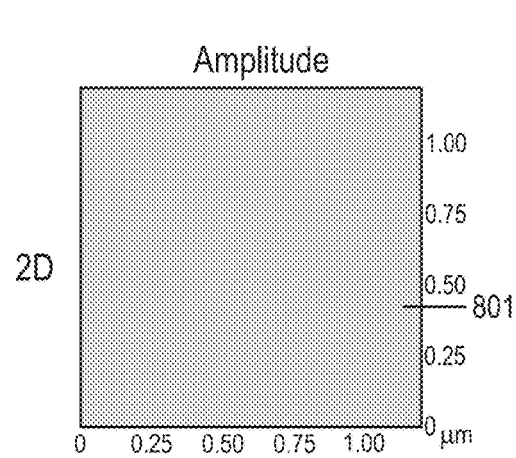
FIGS. 8A and 8B are two- and three-dimensional views of the amplitude of atomic force microscopy (AFM) data generated from a cement according to one embodiment of the present invention.
Figure 8C:
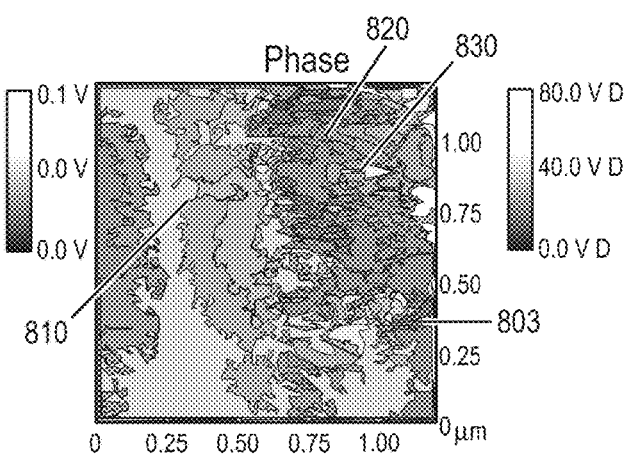
FIGS. 8C and 8D are two- and three-dimensional views of the phase of AFM data generated from a cement according to one embodiment of the present invention.
Figure 8B:
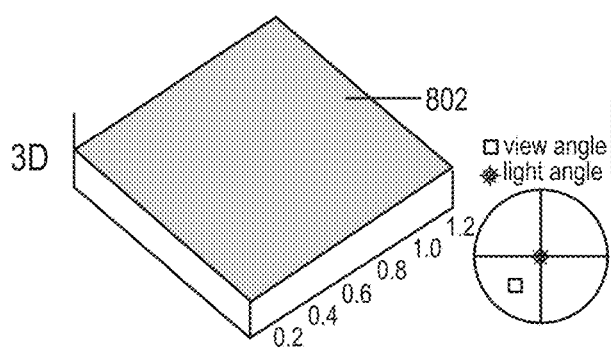
Figure 8D:
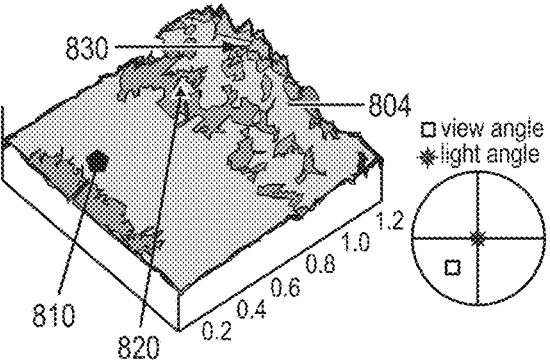
Figure 8E:
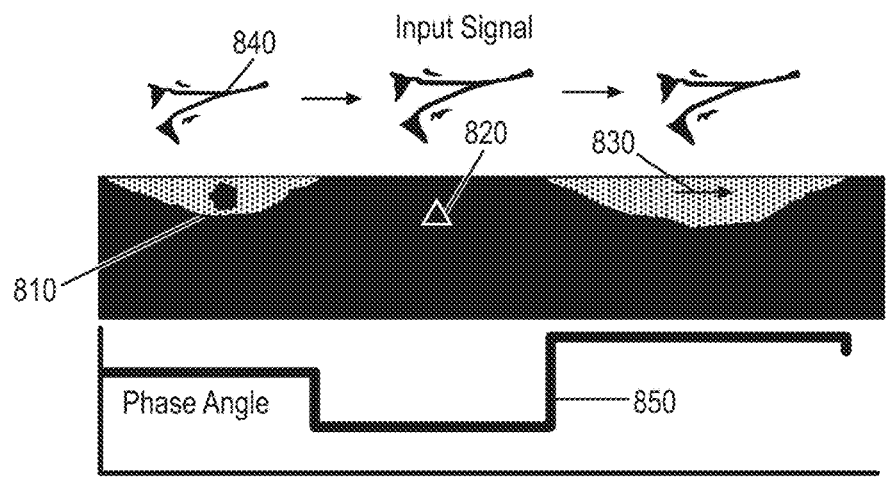
FIG. 8E is a schematic of the material used to generate the AFM data of FIGS. 8A-8D.

The scheme of the amplitude and phase-imaging operation is illustrated in FIG. 8E. The cantilever oscillation depends on the topography and its composition. The amplitude-shift signal changes with variation of sample surface topography, while the phase-shift signal in AM-AFM only changes with variation in the dissipated energy on the sample surface. The image shows three (pentagon 810, triangle 820, and arrow 830) different local regions on the flat substrate. The ACPP gel region (triangle 820) is made of unreacted TTCP (pentagon 810) and newly formed DCPD (arrow 830). Amplitude images in two-dimensional (FIG. 8A) and three-dimensional (FIG. 8B) views shows the smooth surface topology. However, all phase regions will be clearly distinguished from the substrate by recording and plotting the phase signal (see peaks of phase diagrams FIGS. 8C and 8D.)

The topography of the cement investigated by AFM showed a smooth surface by amplitude image (FIGS. 8A and 8B), whereas phase image presented a complex structure with polycrystal blends (FIGS. 8C and 8D). The phase shift only changes with variation in the dissipated energy on the sample surface. The image shows multi-different local regions on the flat substrate (pentagon 810, triangle 820, and arrow 830). The arrow region 830 is made of a different material, and protrudes from the substrate baseline. The triangle region 820 is flat and no obvious boundary displayed, which can be confirmed as ACPP gel phase. The arrows domain 830 shows larger crystal grain size and can be confirmed as well developed DCPD. Thus, the star indicates the unreacted TTCP region. The ACPP gel was infused to TTCP region and more DCPD crystal were growing. Thus, newly formed TTCP crystals were surrounded by ACPP gel, as shown in phase images FIGS. 8C and 8D.

Figure 9:
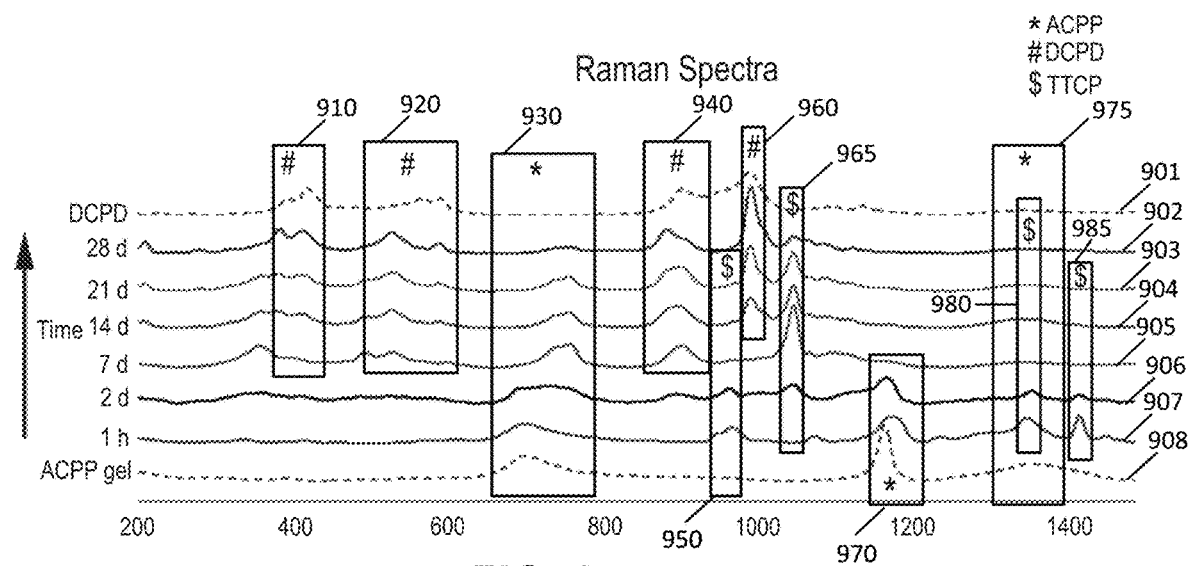
FIG. 9 illustrates Raman spectra of the change in composition of a material according to the present invention over time.

FIG. 9 illustrates the results of Raman spectroscopy studies of polyphosphate cements according to one embodiment of the present invention. To obtain these spectra, an In Vian Raman microscope (Renishaw, Gloucestershire, UK) equipped with a 785 nm excitation laser, 1200 l/mm grating, a 576×400 pixel thermoelectric cooled charge coupled device (CCD), and WiRE 3.3 software were used. A 50×N-plan Leica microscope objective with numeric aperture of 0.75 and working distance of 0.75 mm was used for measurements. At 100% energy, the laser power was approximately 115 mW at the measurement site. Spectra were measured at 10% laser power for three accumulations of 10 seconds each over the spectral range 200 and 1500 cm−1 with spectral resolution varying from 0.87 to 1.11 cm−1. Spectra were acquired on the setting reaction of a cement made from a polyphosphate hydrogel and a calcium and phosphate source, from right after mixing to about 28 days after setting. Following measurement, spectra were processed by background subtraction, vector normalization, spike elimination, and Whitaker smoothing. Several measurements were taken at each time point and averaged to allow for minor variations within the sample or measurement system. Following measurement, spectra were processed by background subtraction, vector normalization, spike elimination, and Whitaker smoothing. Several measurements were taken at each time point and averaged to allow for minor variations within the sample or measurement system.

The Raman spectra illustrate a gradual phase conversion within the cement substrate from ACPP/TTCP to DCPD during incubation at 37° C. and 95% humidity for 28 days. The spectra were taken at different random locations on the cements substrates with laser excitation energy of 1.96 eV. Spectrum 901 represents DCPD alone; Spectrum 908 represents ACPP gel alone. Spectra 902, 903, 904, 905, 906, and 907 were obtained at 1 hour, two days, seven days, 14 days, 21 days, and 28 days, respectively, after mixing.

The broad peaks at 600-800, 1100-1200 and 1300-1400 cm$^{-1}$ correspond to ACPP gel (boxes 930, 970, and 975). The peaks at 940-960, 1030-1050, 1340-1350 and 1410 cm$^{-1}$ correspond to TTCP (boxes 950, 965, 980, and 985). The peaks at 350-420, 530-590, 850-930 and 960-1020 cm$^{-1}$ correspond to DCPD (boxes 910, 920, 940, and 960). ACPP gel (901) and DCPD spectra (908) are included in dash line to show the gradual conversion of the polyphosphate cement over time. Spectra are vertically offset for visual clarity.

For ACPP gel, the first peak (680 cm$^{-1}$; box 930) is assigned to the symmetric vibration of P—O—P bonds, while the second (1180 cm$^{-1}$; box 970) and third (1300 cm$^{-1}$; box 975) regions correspond to the symmetric and asymmetric vibrations of the middle-chain (PO$_2$)$^-$ units, respectively. For TTCP, characteristic brands were assigned at 966, 1066, 1337 and 1440 cm$^{-1}$ (boxes 950, 965, 980, and 985) as v series. For DCPD, characteristic brands were assigned at 412, 562, 900 and 920 cm$^{-1}$ (boxes 910, 920, 940, and 960).

For polyphosphate/calcium phosphate cement at the beginning of incubation, the main band showed as P—O—P and (PO$_2$)$^-$ from ACPP gel and v series from TTCP. Followed by incubation for 28 days, the three groups of ACPP are noticeably affected during incubation: the first band (680 cm$^{-1}$; box 930) becomes broader and shifts to high wavenumber (+30 cm$^{-1}$) while the third one becomes broader and shifts to lower wavenumber (−30 cm$^{-1}$). This can be observed when more calcium content incorporates and act as bridging atom for PP network formation (explained in FIG. 15), which indicates TTCP with abundant calcium coupled with a polyphosphate chain. At the same time, more DCPD peaks start to emerge and developed, while TTCP peaks were decreasing. Until 28 days, most characteristic bands were shown to be DCPD.

Figure 10A:
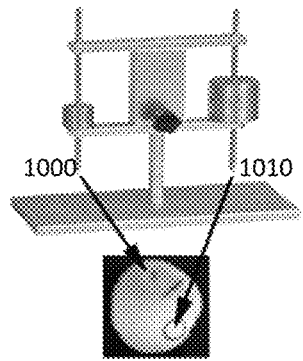
FIGS. 10A and 10B are photographs of experimental setups to test the properties of an injectable bone cement of the present invention.
Figure 10B:
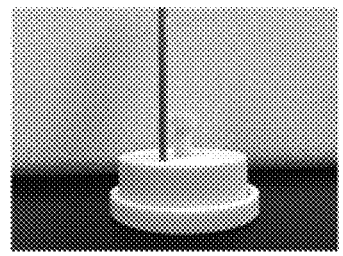
Figure 10C:
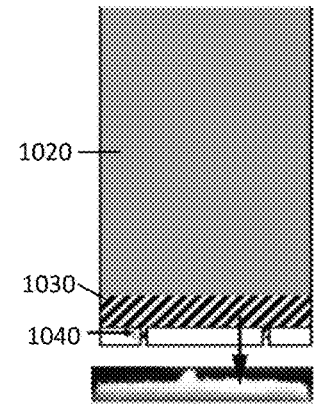
FIG. 10C is a schematic of an experimental setup to test the property of injectability of an injectable bone cement of the present invention.

FIGS. 10A, 10B, and 10C show setups for demonstrating the physical properties of a polyphosphate-containing cement according to one embodiment of the present invention. The Gillmore needle test for set time was performed according to ASTM C266-77. FIG. 10A shows a photograph of the Gilmore needle apparatus. The specimen used was a mortar pat, 3 inches (76.2 mm) in diameter and ½ inch (12.7 mm) in thickness. Initial setting time was measured to represent the setting velocity. Specimen was made to a pat approximately 76 mm (3 inches) in diameter and approximately 13 mm (0.5 inches) in thickness at the center with a flat top and tapering to a thin edge on a clean plane non-absorptive plate. The time of setting was determined by holding the needle in a vertical position and lightly applying it to the surface of the pat. Using the Initial Gillmore needle, the Gillmore Initial setting time end point was determined to be the first penetration measurement that does not mark the specimen surface with a complete circular impression. The initial set was verified by obtaining two additional penetration measurements on different areas of the specimen surface. The elapsed time, in minutes, between the time of contact of cement and mixing water and the end point determined above is the Gillmore initial time of setting. At the initial time of setting, the mass was 113.4±0.5 grams, and the tip diameter was 2.12±0.05 millimeters. In a comparison between an ACPP/TTCP cement made in accordance with the principles of the present invention and a known acrylic PMMA, setting time for the ACPP/TTCP cement was measured to be about 8.17±1.65 minutes, and PMMA was in the 10-15 minute range. Therefore, the polyphosphate/calcium/phosphate cement provides an advantage over PMMA. In other embodiments, the setting time of ACPP/TTCP cement may be from about 1 minute to about 30 minutes, or from about 2 minutes to about 25 minutes, or from about 3 minutes to about 20 minutes, or from about 4 minutes to about 15 minutes, or from about 4 minutes to about 10 minutes, or from about 5 minutes to about 9 minutes, or from about 5 minutes to about 8 minutes, depending on other additives or molecules/cells to be delivered being included, including organic polymers, or inorganic additives among others. In some cases, the setting time may be up to about 30 minutes, or up to about 45 minutes, or up to about 60 minutes, or up to about 90 minutes, or up to about 120 minutes, or up to about 150 minutes, or up to about 180 minutes, or up to about 210 minutes, or up to about 240 minutes, or up to about 300 minutes, or longer.

The ACPP/TTCP compound has physical properties, such as compressive strength (about 60 MPa to about 70 MPa) and Young's modulus (about 1200 MPa), that compare well to PMMA.

FIG. 10B illustrates an experimental setup for an exothermic reaction temperature test. For the test, within 1 min after doughing time, approximately 25 grams of the dough were gently packed into the mold. A thermocouple is positioned with its junction in the center of the mold at a height of 3.0 mm in the internal cavity. The plunger is immediately seated with a C-clamp or suitable press to produce the 6.0 mm specimen height. Upon producing plunger seating, the excess material and the C-clamp or press are removed for the remainder of the procedure. Thereafter, the temperature is continually recorded with respect to time from the onset of mixing the liquid and the powder until cooling is observed. The maximum temperature recorded to the nearest 1° C. is reported. The hole for the thermocouple probe was about 1.6 millimeters (mm) in diameter, and the loaded dough materials had a mass of about 25 grams (g). In a comparison between an ACPP/TTCP cement made in accordance with the principles of the present invention and a known acrylic PMMA, setting temperature for the ACPP/TTCP cement was measured to be about 31.7±0.3 degrees Celsius, and PMMA was in the 80-90 degrees Celsius range. The setting temperature of the polyphosphate/calcium/phosphate cement is therefore about 25 degrees Celsius to about 37 degrees Celsius, or about 27 degrees Celsius to about 35 degrees Celsius, or about 30 degrees Celsius to about 34 degrees Celsius, or about 31 degrees Celsius to about 33 degrees Celsius, or about 32 degrees Celsius. Therefore, the polyphosphate/calcium/phosphate cement has an exothermic setting temperature far closer to physiological temperature and provides an advantage over PMMA.

FIG. 10C shows a schematic view of an apparatus for an injectability test. An intrusion die was manufactured following ASTM F451-08. Following the set, dough 1030 was loaded to the cylindrical mold (white portion of FIG. 10C) and mortarpat 1020 was placed on the top. Once the dough reaches equilibrium, the specimen is removed, and the average height of the intrusion into all four of the 1.0-mm diameter holes 1040 of the die is measured. Across three measurements, the ACPP/TTCP cement had an injectability of 1.08±0.05 mm, which is virtually identical to the result of 1.03±0.07 mm attained from injection of PMMA, which is known to be a highly injectable material.

FIG. 11A-FIG. 11E illustrate a cohesion test and its results, principally contrasting the cohesive properties of a polyphosphate cement with those of a traditional CPC. Samples were mixed according to the ratio of 1:0.87 ACPPgel:TTCP based on the previous setting time measurements. To maintain consistency between groups an equal volume of ACPP gel and MCPM solution were used to obtain a modified formula of 0.64 ml to 0.87 g MCPM solution to TTCP powder. The MCPM solution was a saturated solution containing approximately 40 mg/ml MCPM. When a well-mixed ACPP/TTCP cement is injected into a cylinder of water, as shown in FIG. 11A, it maintains the shape it had when injected, that is a cohesive ribbon 1101 of material in the column of water. In contrast, the traditional CPC shown in the photograph of FIG. 11B has a more disperse structure 1102.

As shown in FIGS. 11C and 11D and quantified in FIG. 11E, following mixing, samples were molded into cylindrical shapes of roughly 10 mm diameter and 5 mm height. After curing the samples were submerged into PBS at room temperature and left undisturbed. The specimens were mixed according to the ratio of 1:0.87 ACPP gel:TTCP. Following mixing, samples were molded into cylindrical shapes of roughly 10 mm diameter and 5 mm height. After curing the samples were submerged into PBS at room temperature and left undisturbed. Samples were allowed to dry for approximately 24 hours before recording mass following immersion.

After approximately 72 hours the PBS had evaporated and left salt residue behind. However, up until that point there were only small aggregates of lost particles in the ACPP samples (1112, bottom rows of FIGS. 11C and 11D), but noticeable particles lost in all of the MCPM samples (1111, top rows of FIGS. 11C and 11D)—particularly in the leftmost specimen. Sample masses were measured prior to and post immersion in PBS. Samples were allowed to dry for approximately 24 hours before recording mass following immersion. Weight loss was presented as: Weight loss percent is calculated using the formula $(W1-W2)/W1\times100$. Weight loss is illustrated in FIG. 11E. Whereas the traditional CPC discs 1130 lost 2.5% of their weight within 72 hours, the polyphosphate/calcium/phosphate cement 1120 prepared in accordance with the principles of the present invention lost on average only about 0.5% of their weights.

From the quantitative cohesion test, both the inventive cement and CPC specimen appeared to retain integrity initially. After approximately 72 hours, only small aggregates of particles can be viewed nearby ACPP samples 1112, but noticeable particles precipitates were accumulated around CPC samples 1111. Based on visual evidence the ACPP samples retain their material better than CPC specimen. Mass change calculations indicate more CPC compartment was washing out while polyphosphate/calcium/phosphate showed better water-resistance after setting.

Figure 12:
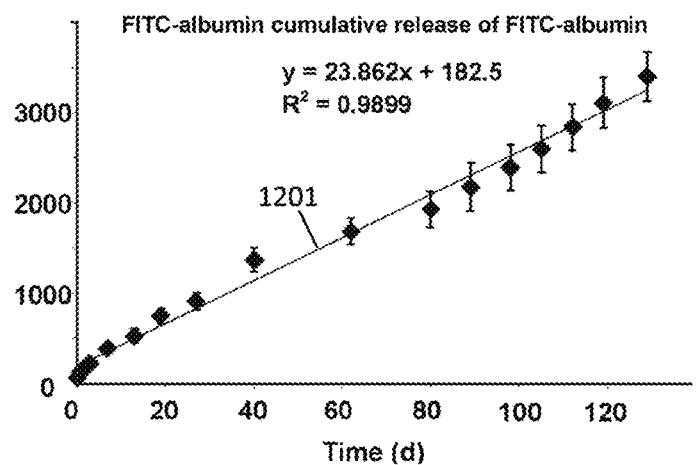
FIG. 12 is a plot of release of a protein from a material according to one embodiment of the present invention.

FIG. 12 demonstrates that proteins can be stored in and delivered in controlled fashion by a polyphosphate/calcium/phosphate cement according to the principles of the present disclosure. FIG. 12 shows in vitro release of albumin from an ACPP/TTCP scaffold which was subjected to in vitro release conditions by immersion in 1 mL of $DH_2O$ medium in sealed polystyrene tubes. Samples were continuously agitated in a water bath (36.5±0.5° C.) over 130 days. At each time point, aliquots of soaking medium were removed for Albumin-FITC measurement, and the removed simulated body fluid (SBF) was replaced by the same amount of fresh SBF. The concentration of albumin from the collected medium was measured spectrophotometrically using a fluorescence method. Medium was then measured using a UV/VIS Spectrophotometer at wavelength of 586 nm. The standard OD-concentration curve was drawn by measuring gradient albumin-FITC solutions. FIG. 12 shows the drug loading and releasing capability of a polyphosphate cement after solidification. FITC-albumin, was mixed with ACPP before gel preparation and the final EM concentration in the CPP mix was about 5% (w/w). As shown, albumin release is stable and constant, maintaining the zero-order release at least up to about 130 days. With protein release related to conversion of the cement to its end product, it is expected that release continues through the entire conversion process, which for certain embodiments can be up to about 365 days.

Figure 13A:
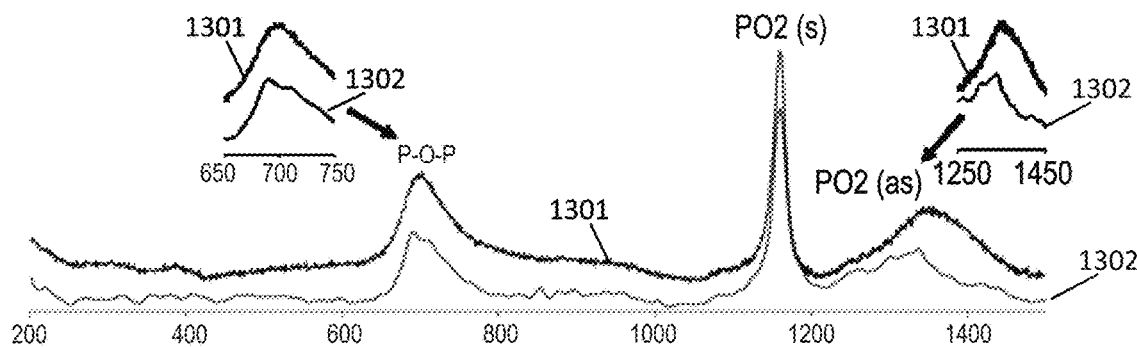
FIGS. 13A and 13B are Raman spectra illustrating the dynamic changes of interaction between a protein and a material of the present invention during mixing.
Figure 13B:
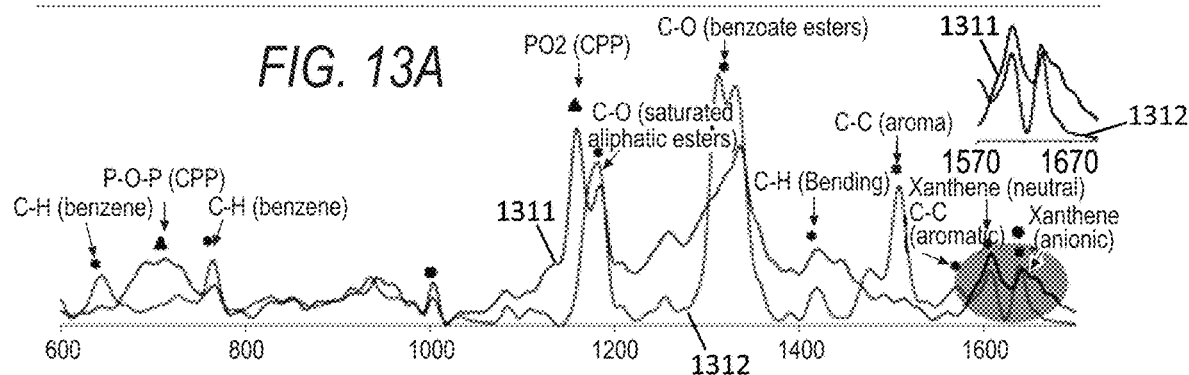

FIGS. 13A and 13B are Raman spectra showing the dynamic changes of interaction between albumin-FITC and ACPP gel during mixing. Raman spectra of ACPP (1301) and ACPP/albumin (1302) are shown. A schematic illustration of the bonding of FITC-albumin and ACPP is shown in FIG. 16D. FITC-albumin in this experiment, was loaded into the ACPP/TTCP cement mainly through coupling with ACPP network, which is confirmed by Raman shift. As shown, the upward P—O—P (700 $cm^{-1}$) and downward $PO_2^-$ (1300 $cm^{-1}$) unit shift from ACPP, as discussed previously, was influenced by polyphosphate chain conformation in response to the albumin-FITC incorporate and network formation.

As shown in FIG. 13B, an albumin-FITC sample 1312 and albumin-FITC in ACPP/TTCP gel sample 1311 were subjected to Raman spectroscopy. Most characteristic peaks were from FITC (1311). After mixing, both ACPP (triangle,) and FITC (star) peaks were observable. Notably, the presence of two peaks (1610 $cm^{-1}$ and 1640 $cm^{-1}$, ellipse) from xanthene indicated both anion and neutral forms of FITC in the mixture. Either form provides the COO— bindings to chelated calcium from the ACPP gel. It was also confirmed that coupled FITC showed major reduction of aromatic C—C peaks (1510 $cm^1$) due to the depolarization of benzene ring with COOH.

FIGS. 14A and 14B show the results of a RAW macrophage cells eluent culture experiment according to an ASTM standard which illustrates that the polyphosphate/calcium/phosphate cement of the present disclosure is biocompatible and not cytotoxic when used in conjunction with viable and proliferating cells. The immortalized osteoblastic RAW264.7 cell line from murine macrophage was used in this study. These cells were incubated in humidified atmosphere of 5% $CO_2$ at 37° C. Cells were cultured in Dulbecco's modified Eagle's medium (DMEM) supplemented with 10% fetal bovine serum (FBS, Hyclone, Logan, Utah), 2 mM L-glutamine, and 1% (v/v) antibiotics mixture(10,000 U of penicillin and 10 mg of streptomycin). The culture media was changed every 48 h. Post-setting ACPP/TTCP cement specimens were dried and soaked in 0.9% saline for 120 hours at 37° C. to extract the soluble components. RAW cells were seeded into a 24 well plate and allowed to attach for 2 hours. Following 2 hours the media was supplemented with 5% of the material eluent and allowed to grow for 1 week. Time points were taken at 3 and 7 days changing media every 2 days. Cell number was analyzed using the Picogreen DNA assay. Cytotoxic effects were measured by determining the LDH concentration in the media. The cement samples were placed in the incubator for 4 weeks to allow conversion to DCPD. Following the 4 weeks the powders were dried and soaked in 0.9% saline for 120 hours at 37° C. to extract the soluble components. In addition to incubated samples, freshly prepared samples were also soaked. RAW cells were seeded into a 24 well plate and allowed to attach for about 2 hours. Following 2 hours the media was supplemented with 5% of the material eluent and allowed to grow for 1 week. Time points were taken at 3 and 7 days changing media every 2 days. In FIG. 14A, cell number was analyzed using the Picogreen DNA assay. In FIG. 14B, cytotoxic effects were measured by determining the LDH concentration in the media. The eluent of the polyphosphate/calcium/phosphate cement cultured with RAW cells shows better cell proliferation rate during culturing period in comparison of experimental control (saline), and the cytotoxicity of ACPP/TTCP is also less compared to control (FIG. 14B).

Throughout the disclosure, statistical comparisons between means were made by Student's t-test (SPSS 16, SPSS). A p-value of less than 0.05 was considered statistically significant. Data were analyzed with SPSS Version 22.0 (IBM, Armonk, N.Y.). All values are expressed as mean±standard deviation. Analysis of Variance (ANOVA) was used to analyze the experimental data from all the experiments. Statistical significance was set to $p<0.05$.

Figure 15:
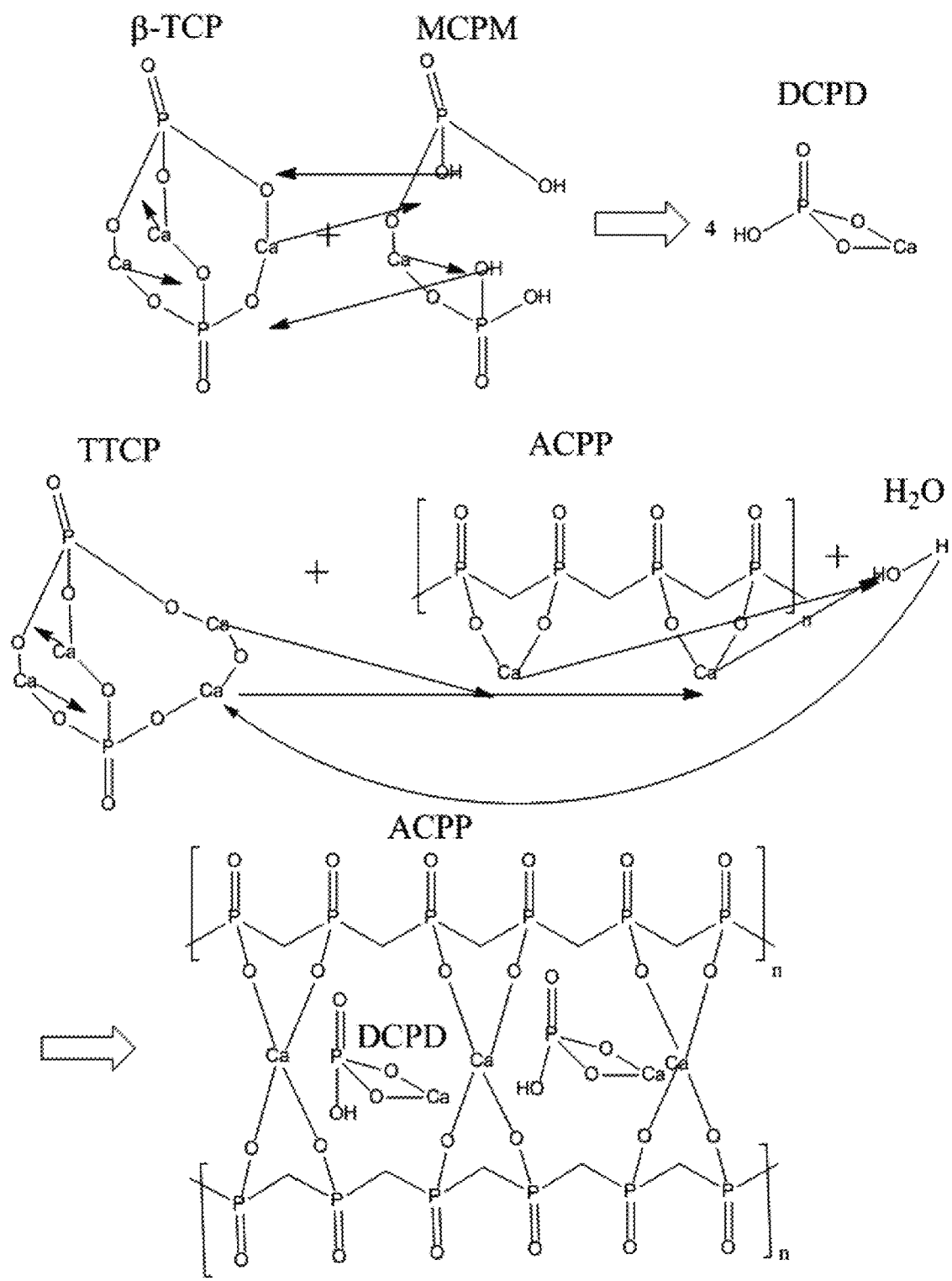
FIG. 15 is a schematic illustrating one possible mechanism for the formation of a material according to one embodiment of the present invention.

FIG. 15 illustrates the mechanism by which the components of a cement made according to the principles of the present disclosure may interact to form the cement having optimized properties. It is noted that calcium and other multivalent cations interact strongly with the linear polyphosphate polyanion molecules, which can result in the formation of a viscous solution or hydrogel. The multivalent cations can bridge between linear polyphosphate chains, effectively forming a bridged network polymer. Physical data show that the hydrogel can have linear and cyclic polyphosphate structures consisting of phosphate groups connected to calcium ions and protons of hydrogen-bonded water molecules. The polyphosphate chains of the substance entangle with one another, leading to the formation of a three-dimensional network structure via ionic bonding and chain entanglement. Increase in water supply may increase gel properties of a polyphosphate-containing composition.

Polyphosphate powders transform into a hydrogel before the ions dissociate completely into deionized water. Polyphosphate gelation is believed to proceed by two mechanisms: intermingling of polyphosphate chains from neighboring polyphosphates, and divalent cation (such as calcium) crosslinking or chelation between the polyphosphate chains within the polyphosphate gel matrix of two neighboring particles. The divalent cations are able to bond with the non-bridging oxygens (that is, those not in the P—O—P backbone of a polyphosphate molecule). Monovalent cations also influence the properties of the formulation through ion-substitution.

Taken together, this disclosure provides a process for the conversion of a polyphosphate, in one instance amorphous calcium polyphosphate, with a calcium and phosphate source, in one instance tetracalcium phosphate, to a new product over time, in one case dicalcium phosphate dihydrate, in a liquid environment. The calcium and phosphate source is provided as a powder and is mixed with a hydrogel of the polyphosphate. In the case of an ACPP/TTCP combination, the resultant cement is less brittle than a conventional calcium phosphate cement, is able to provide prolonged release of drug, and yields low mechanical-strength and undegradable end products, such as hydroxyapatite.

In contrast, an injectable bone cement made from a first polyphosphate compound in hydrogel form and a second calcium and phosphate source, the second source in some embodiments not being a calcium polyphosphate, can yield a biodegradable end product, such as DCPD, the degradation rate of which can be controlled to match the physiological parameters of bone remodeling, by, for example, adjusting the ratio of polyphosphate compound and calcium/phosphate source (higher polyphosphate content would speed up the degradation and vice versa). Further, a polyphosphate hydrogel-based cement may be used to deliver substances (drugs, proteins, cells) owing to the interaction of these substances with the hydrogel matrix by ionic bonding and physical trapping. The combination of polyphosphate and calcium and phosphate components creates an osteoinductive cement, as opposed to conventional calcium phosphate cements, which in general have very low osteogenesis properties. The DCPD molecules which form may intercalate between polyphosphate chains, as shown in FIG. 15.

FIGS. 16A, 16B, and 16C contrast the mechanisms of formation of conventional CPCs (FIG. 16A) and the polyphosphate/calcium/phosphate cements of the present disclosure (FIGS. 16B and 16C).

In the classical mechanism of FIG. 16A, MCPM 1601 combines with beta-TCP 1602 in mixing step 1604 and setting step 1605 to produce DCPD monomers or particles 1603. FIG. 16B shows that the polyphosphate composition also results in DCPD formation, but there is a network of polyphosphates which combines to provide advantageous mechanical, chemical, and physiological properties. FIG. 16B shows that polyphosphate gel 1611 combines with TTCP particles 1612 in mixing step 1614 and setting step 1615 to entrap the TTCP particles 1612 within the hydrogel matrix of the polyphosphate 1611, where after hours, days, or weeks of reaction time, the formation of a DCPD-polyphosphate 1613 is realized. FIG. 16C shows the specific mechanism of ACPP/TTCP interaction and partial conversion to DCPD. Thus, as shown in FIGS. 16A-16C, the "grapes on a stem" configuration of the cement as described herein can be contrasted with the monomer-plus-monomer configuration of the prior art CPC. Without wishing to be bound by any particular theory, the water in the hydrogel dissolves the calcium and phosphate source, such as TTCP, and such dissolution allows for the entry of the various components, particularly the calcium atoms, to dissolve into the polyphosphate matrix itself, causing precipitation and eventual solidification as the water is eliminated. This differs greatly from the setting mechanism of classical CPC, which is based on crystallization unrelated to intra/inter-molecular dehydration of the hydrogel within polymeric phosphate chains. The cement setting via such a dehydration mechanism represents a previously unknown mechanism for a cement capable of bone repair applications. In one embodiment, the hydrogel can supply water molecules that hydrate the polyphosphate hydrogel to the source of calcium and phosphate, allowing it to convert to a different product (in one embodiment, DCPD) and as the hydrogel loses water molecules, the cement sets thereby.

Without wishing to be bound by any particular theory, the embodiment that has been described through this disclosure is ACPP with TTCP. It is to be noted that many different polyphosphates, including polyphosphate salts, will work to provide a suitable structure for hydrogel formation. In particular, divalent-cation containing salts of polyphosphates are envisioned. Further, calcium and phosphate sources other than TTCP may be used, which may in turn lead to the formation of other final products. TTCP was chosen as the compound DCPD eventually arises from TTCP incubation in an ACPP hydrogel. Further, as both ACPP and TTCP have a calcium phosphate component, using both provides phase compatibility.

The ACPP/TTCP compound has physical properties, such as compressive strength (about 60 MPa to about 70 MPa) and Young's modulus (about 1200 MPa), that compare well to PMMA. These physical properties also compare better than those of classical CPCs. For example, a classical CPC may only have compressive strength of about 5 MPa to about 20 MPa, and Young's modulus of only about 400. Further, a classical CPC may take double or triple the time to set compared to the polyphosphate cement (in one embodiment, about 15 minutes versus about 5 minutes to about 8 minutes). The classical CPC may have significantly lower washout resistance compared to the polyphosphate cement (about 40% to about 99.5%) and drug release of a classical cement is limited to a week or less, compared to multiple months for polyphosphate cement.

Further, the setting temperature of these polyphosphate/calcium/phosphate cements is lower than acrylics like PMMA. PMMA must be mixed a significant amount of time prior to usage, as mixing is exothermic and the setting temperature of about 80 degrees Celsius is dangerously about physiological temperature, and thus the cement must cool before implantation. Immediate injection can also cause complications which can be potentially deadly, such as pulmonary embolism. In contrast, the polyphosphate hydrogel/calcium/phosphate cements as described herein have setting temperatures of about 0° C. to about 75° C., or about 5° C. to about 70° C., or about 10° C. to about 60° C., or about 15° C. to about 50° C., or about 17° C. to about 45° C., or about 20° C. to about 42° C., or about 22° C. to about 42° C., or about 25° C. to about 40° C., or about 30° C. to about 40° C., or about 35° C. to about 40° C., or about 37° C. to about 42° C., or about 37° C. to about 40° C., or about 37° C. The cement of the present invention can be injected within about 0 minutes to about 10 minutes of mixing, or within about 1 minute to about 8 minutes, or about 2 minutes to about 5 minutes of mixing, or immediately after mixing.

The cements of the present disclosure have physical properties of polymers. In some embodiments, a second polymer (other than the polyphosphate) may be added to the cement. Such a polymer may be an organic polymer, and may influence the physical properties of the cement. The data as provided herein are exemplary of an embodiment which does not include a second polymer. However, a second polymer is within the scope of this invention. Examples of polymers envisioned for inclusion in this way include a polycarboxylate, a polysulfate, polysulfonates, a polyphosphate, a polyamine, a polyurea, a polyamide, a polyalkylene oxide diol, a polyalkylene oxide diamine, a polycarbonate, a polylactone, a polyethersulfone, a polyvinyl, a polypeptide, a polysaccharide, a polyurethane, a polysulfone, a polycarbonate, a polyester, polyethylene, polypropylene, polystyrene, polysilicone, poly(acrylonitrile-butadienestyrene), polybutadiene, polyisoprene, polymethyl methacrylate, polyvinylacetate, polyacrylonitrile, polyvinyl chloride, polyethylene terephtalate, cellulose, a polysilicone, a polyolefin, a polyvinyl derivative, a polypeptide derivative, poly(lactic-co-glycolic acid), and a polysaccharide derivative, among others. It will be appreciated that the properties, including viscosity, injectability, mechanical strength, and the like will be altered by incorporation of an additional material into the polyphosphate/calcium/phosphate cement.

Over time, the DCPD itself may be converted. One potential fate of DCPD is to become, at least in part, hydroxyapatite and/or calcium deficient hydroxapatitite (CDHA). The first and primary product of setting is DCPD for the polyphosphate-based cements disclosed herein.

Moreover, the polyphosphate hydrogel/calcium/phosphate cements of the present disclosure will provide mechanical strengths comparable to those of native bone, and the cements may find use in load-bearing applications, which conventional CPC has not been able to achieve.

The invention claimed is:

1. A cement comprising:
   a hydrogel including a polyphosphate selected from the group consisting of sodium polyphosphate, potassium polyphosphate, calcium polyphosphate, strontium polyphosphate, magnesium polyphosphate, aluminum polyphosphate, zinc polyphosphate, copper polyphosphate, cadmium polyphosphate, manganese polyphosphate, and ammonium polyphosphate, and
   tetracalcium phosphate,
   wherein a ratio of the hydrogel to tetracalcium phosphate is 1:0.1 to 1:10 by weight,
   wherein the cement is injectable and has a mechanical strength for a bone repair application.

2. The cement of claim 1, wherein the cement has a setting mechanism comprising reaction of dehydration of the hydrogel.

3. The cement of claim 1 wherein the polyphosphate has a degree of polymerization of at least about 2.

4. The cement of claim 1 wherein the mechanical strength comprises a compressive strength of between about 5 megapascal and about 200 megapascal.

5. The cement of claim 1 further comprising at least one of an inorganic filler and an organic filler.

6. The cement of claim 5 wherein the inorganic filler comprises at least one of a bioglass, a silica ceramic, an oxide ceramic, a carbon fiber, a metal, and a metal alloy.

7. The cement of claim 5 wherein the inorganic filler comprises a powder having a particle size of about 1 nanometer to about 1000 micrometers.

8. The cement of claim 5 comprising at least one of a polycarboxylate, a polysulfate, polysulfonates, a polyphosphate, a polyamine, a polyurea, a polyamide, a polyalkylene oxide diol, a polyalkylene oxide diamine, a polycarbonate, a polylactone, a polyethersulfone, a polyvinyl, a polypeptide, a polysaccharide, a polyurethane, a polysulfone, a polyester, polyethylene, polypropylene, polystyrene, polysilicone, poly(acrylonitrile-butadienestyrene), polybutadiene, polyisoprene, polymethylmethacrylate, polyvinylacetate, polyacrylonitrile, polyvinyl chloride, polyethylene terephtalate, cellulose, a polysilicone, a polyolefin, a polyvinyl derivative, a polypeptide derivative, poly(lactic-co-glycolic acid), and a polysaccharide derivative.

9. The cement of claim 5, comprising at least one of a carboxylate, a sulfate, a sulfonate, a phosphate, an amine, urea, an amide, an alkylene oxide diol, an alkylene oxide diamine, a carbonate, a lactone, an ethersulfone, a vinyl, a peptide, a dimethacrylate, a saccharide, a urethane, a sulfone, an ester, an ethylene, propylene, a styrene, silicone, acrylonitrile-butadienestyrene, butadiene, an isoprene, methylmethacrylate, vinylacetate, acrylonitrile, vinyl chloride, ethylene terephtalate, an olefin, a vinyl derivative, bisphenol A, a bisphenol A derivative, an oligosaccharide, a peptide derivative, lactic acid, glycolic acid, cyanoacrylate, a cyanoacrylate derivative, and a saccharide derivative.

10. The cement of claim 1 having a setting time from 1 minute to about 30 minutes.

11. The cement of claim 1 having a ratio of calcium to phosphate of about 1:10 to about 10:1.

12. The cement of claim 1, wherein the polyphosphate is an amorphous polyphosphate.

13. The cement of claim 12, comprising amorphous calcium polyphosphate.

14. The cement of claim 1, wherein the ratio is 1:0.15 to 1:1.

15. A method of making an injectable bone cement, the method comprising:
    gelating a polyphosphate compound in aqueous solution to form a hydrogel, the polyphosphate compound being selected from the group consisting of sodium polyphosphate, potassium polyphosphate, calcium polyphosphate, strontium polyphosphate, magnesium polyphosphate, aluminum polyphosphate, zinc polyphosphate, copper polyphosphate, cadmium polyphosphate, manganese polyphosphate, ammonium polyphosphate; and
    reacting the hydrogel with tetracalcium phosphate wherein the ratio of the hydrogel to tetracalcium phosphate is 1:0.1 to 1:10 by weight, to form the injectable bone cement.

16. The method of claim 15 further comprising mixing a filler material with the polyphosphate compound, the filler material comprising at least one of an inorganic material and an organic material.

17. The method of claim 15, wherein the first polyphosphate compound comprises amorphous calcium polyphosphate.

18. The method of claim 15, comprising at least one of a polycarboxylate, a polysulfate, polysulfonates, a polyphosphate, a polyamine, a polyurea, a polyamide, a polyalkylene oxide diol, a polyalkylene oxide diamine, a polycarbonate, a polylactone, a polyethersulfone, a polyvinyl, a polypeptide, a polysaccharide, a polyurethane, a polysulfone, a polyester, polyethylene, polypropylene, polystyrene, polysilicone, poly(acrylonitrile-butadienestyrene), polybutadiene, polyisoprene, polymethylmethacrylate, polyvinylacetate, polyacrylonitrile, polyvinyl chloride, polyethylene terephtalate, cellulose, a polysilicone, a polyolefin, a polyvinyl derivative, a polypeptide derivative, poly(lactic-co-glycolic acid), and a polysaccharide derivative.

19. The method of claim 15, comprising at least one of a carboxylate, a sulfate, a sulfonate, a phosphate, an amine, urea, an amide, an alkylene oxide diol, an alkylene oxide diamine, a carbonate, a lactone, an ethersulfone, a vinyl, a peptide, a dimethacrylate, a saccharide, a urethane, a sulfone, an ester, an ethylene, propylene, a styrene, silicone, acrylonitrile-butadienestyrene, butadiene, an isoprene, methylmethacrylate, vinylacetate, acrylonitrile, vinyl chloride, ethylene terephtalate, an olefin, a vinyl derivative, bisphenol A, a bisphenol A derivative, an oligosaccharide, a peptide derivative, lactic acid, glycolic acid, cyanoacrylate, a cyanoacrylate derivative, and a saccharide derivative.

20. The method of claim 15, wherein the ratio is 1:0.15 to 1:1.

\* \* \* \* \*